United States Patent [19]
Hale et al.

[11] Patent Number: 5,622,944
[45] Date of Patent: Apr. 22, 1997

[54] TESTOSTERONE PRODRUGS FOR IMPROVED DRUG DELIVERY

[75] Inventors: Ron L. Hale, Woodside; Amy T. Lu, Los Altos; Dennis W. Solas, San Francisco; Michel J. N. Cormier, Mountain View, all of Calif.

[73] Assignees: Affymax Technologies N.V., Middlesex, England; Alza Corporation, Palo Alto, Calif.

[21] Appl. No.: 434,892

[22] Filed: May 4, 1995

Related U.S. Application Data

[63] Continuation-in-part of Ser. No. 898,219, Jun. 12, 1992, abandoned, and Ser. No. 77,296, Jun. 14, 1993, abandoned, which is a continuation-in-part of Ser. No. 898,219, and Ser. No. 9,463, Jan. 27, 1993, abandoned.

[51] Int. Cl.⁶ .................................................. A61K 31/575
[52] U.S. Cl. ........................ 514/181; 514/177; 514/178; 514/179; 514/180; 604/20
[58] Field of Search .................................... 514/177–181; 604/20

[56] References Cited

U.S. PATENT DOCUMENTS 5,068,226 11/1991 Weinshenker et al. .................... 514/58

FOREIGN PATENT DOCUMENTS 9008128 7/1990 WIPO.

OTHER PUBLICATIONS

Bodor et al. Improved Delivery Through Biological Membranes XXII—Int. J. Pharmaceutics 35(1987) pp. 47–59.
Banga et al Iontophoretic Delivery of Drugs: Fundamentals Developments and Biomedical Applications—J. of Controlled Release 7 (1988) 1–24.

Primary Examiner—Neil S. Levy
Attorney, Agent, or Firm—Lauren L. Stevens

[57] ABSTRACT

Compositions and methods are provided for enhanced transdermal electrotransport of 17-hydroxy sterol compounds, including testosterone. The parent sterols are modified at the 17-hydroxy position by covalent attachment of a charged chemical modifier. The chemical modifier provides the parent sterol with enhanced transport properties and is hydrolyzed under physiological conditions to release the active parent compound.

The composition comprises a 17-hydroxy sterol/chemical modifier complex, more generally represented by the formula (sterol—O—)C(O)—R—N($R^1$)($R^2$)($R^3$)⁺. The portion of the complex derived from the chemical modifier is indicated by "C(O)—R—N($R^1$)($R^2$)($R^3$)⁺", where N($R^1$)($R^2$)($R^3$)⁺ represents a quaternary ammonium group and $R^1$, $R^2$, and $R^3$ are independently selected from the group consisting of lower alkyl, alkyl, aryl, arylalkyl, cycloalkyl, heteroalkyl, and heteroarylalkyl; or $R^1$ and $R^2$ together with the nitrogen to which they are attached form a substituted heterocycle and $R^3$ is lower alkyl, and R is a linking moiety, linking the (sterol—O)—C(O)— to the nitrogen atom.

14 Claims, 8 Drawing Sheets

Fig. 1a
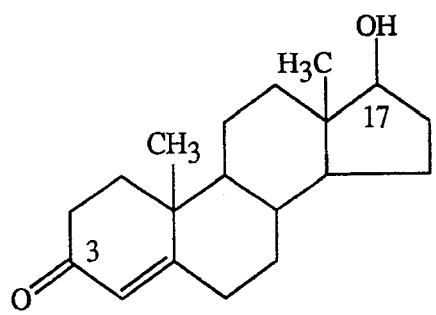
Fig. 1b
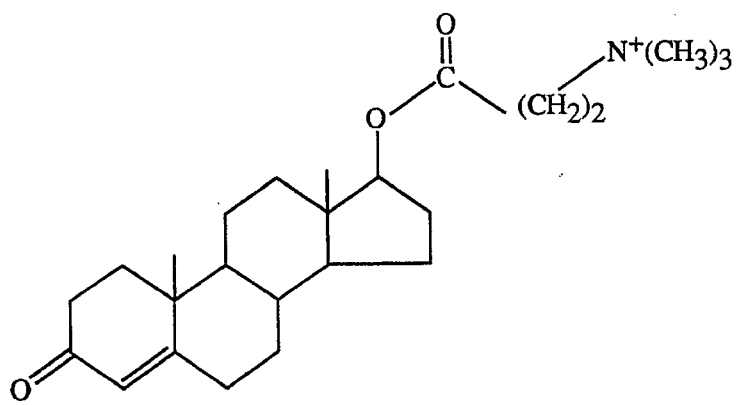
Fig. 1c
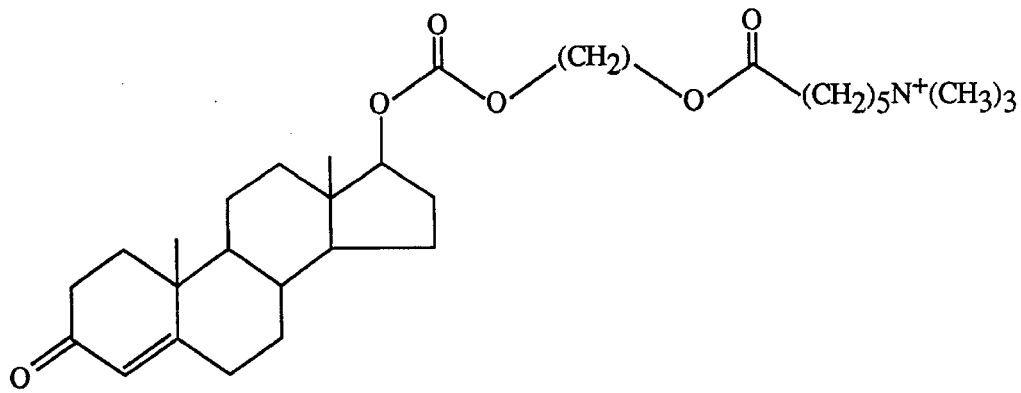
Figure 1a-1c

Fig. 1d
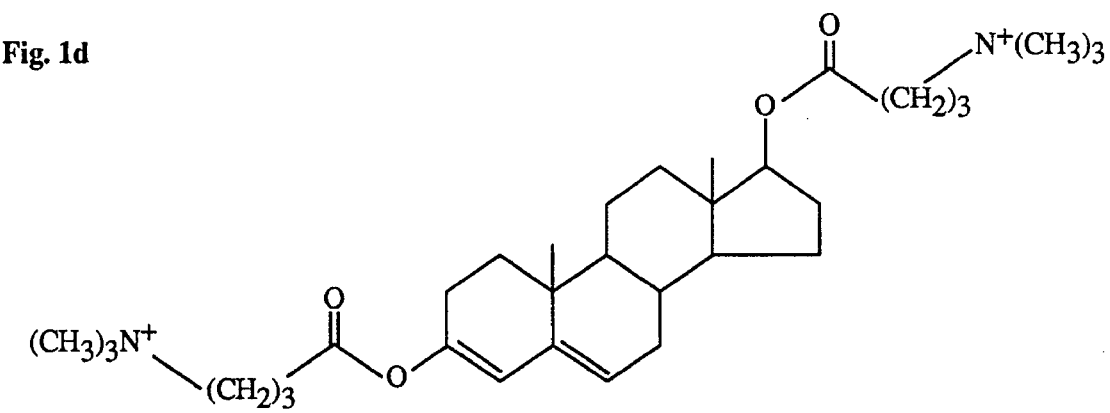
Fig. 1e
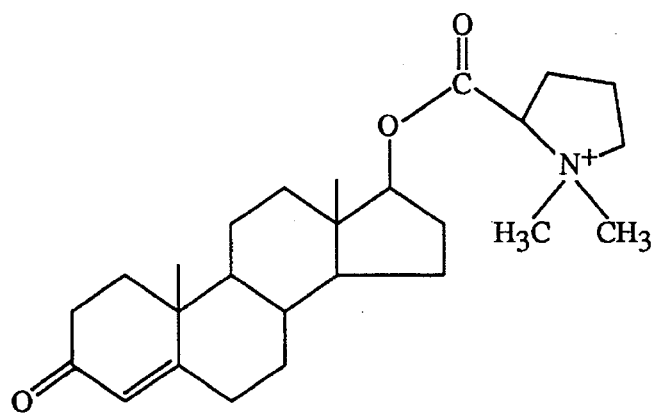
Fig. 1f
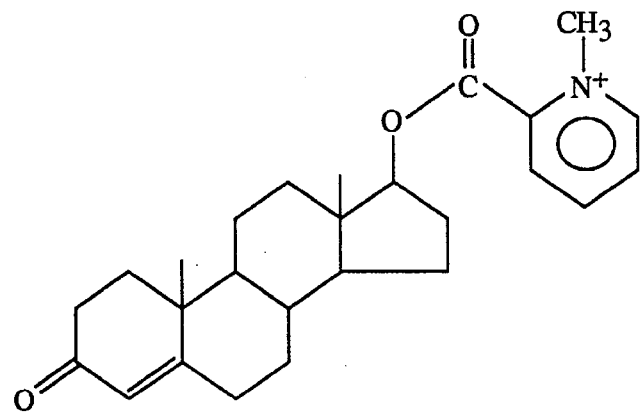
Figures 1d-1f

TESTOSTERONE PRODRUGS FOR IMPROVED DRUG DELIVERY

This application is a continuation-in-part of application Ser. No. 07/898,219, filed Jun. 12, 1992, now abandoned. This application is also a continuation-in-part of application Ser. No. 08/077,296, filed on Jun. 14, 1993, now abandoned which is a continuation-in-part of application Ser No. 07/898,219 and application Ser No. 08/009,463, filed on Jan. 27, 1993, now abandoned. Both of the above identified applications are incorporated herein by reference.

FIELD OF THE INVENTION

The present invention relates to prodrugs of 17-hydroxy sterols, particularly testosterone, for improved transdermal delivery.

REFERENCES

Anderson, K. E., et al., *Contact Dermatitis* 16: 55–78 (1987).

Banga, A. K. and Chien, Y. W., *J. Controlled Release* 7: 1–24 (1988).

Brendel, et al., *Biochem. Biophys. Acta* 137: 8 (1967).

Goldfien, A., In: *BASIC AND CLINICAL PHARMACOLOGY* (Katzung, B. G., Ed.) Appleton & Lange, Norwalk, Conn., pp. 461–483 (1987).

Griffin, J. E. and Wilson, J. D., In: *HARRISON'S PRINCIPLES OF INTERNAL MEDICINE*, 12th Ed., (Harrison, T. R., et al., Eds.), McGraw-Hill, Inc., New York, N.Y., pp 1765–1776 (1991).

Guy, R. and Hadgraft, J., In: *TRANSDERMAL DRUG DELIVERY: DEVELOPMENTAL ISSUES AND RESEARCH INITIATIVES*, Vol 35, (Guy, R., et al., Eds.), Marcel Dekker, Inc., New York, N.Y., pp. 59–77 (1989).

Pratt, W. B.; et al., Eds., In: *PRINCIPLES OF DRUG ACTION: THE BASIS OF PHARMACOLOGY*, 3rd ed., Churchill Livingstone Inc., New York, N.Y., pp 203–227 (1990).

Steinberg, M., In *CUTANEOUS TOXICITY* (Drill, V. A. and Lazar P., Eds.), Raven Press, New York, N.Y., p. 4153 (1984).

Swisher, D., et al., *Models in Dermatology* 4: 131–137 (1989).

Wade, L., In: *COMPENDIUM OF ORGANIC SYNTHETIC METHODS*, Vol 5., John Wiley & Sons, New York, N.Y. (1984).

BACKGROUND OF THE INVENTION

Steroid hormones, such as the estrogens and the androgens, represent an important class of clinically administered compounds. Estrogens are used extensively for replacement therapy, treatment of hypogonadism, and contraception. The androgens, and particularly testosterone, are used in replacement therapy, treatment of gynecologic disorders, as protein anabolic agents, and as metabolic stimulators.

When administered orally, testosterone is readily absorbed but is rapidly degraded by the liver so that only insignificant amounts reach the systemic circulation. When administered intramuscularly, testosterone is promptly absorbed from the injection vehicle, metabolized and excreted, making it difficult to achieve sustained, effective plasma levels.

Modified forms of testosterone have been developed for intramuscular use which are more soluble in the injection vehicle and are more slowly absorbed from the site of injection. The depot of drug thus provides a more sustained delivery of drug to the circulation. However, in many cases, injection is an undesirable form of drug administration due to its invasive nature, predisposition of the administration site to infection, and the potential painfulness of the procedure. Additionally, injection causes an initial high plasma level of drug which steadily decreases until the next injection.

An alternative which overcomes many of these difficulties is to administer such compounds transdermally. However, transdermal administration is often hampered by the fact that the skin is an efficient barrier to the ingress of materials. Very few therapeutic agents penetrate the skin at rates which allow the delivery of therapeutically effective amounts of drug.

Although many chemical penetration enhancers have been identified which may increase a compound's ability to penetrate the skin, the process of selecting a suitable enhancer system is often long and laborious, and many times unsuccessful. Many penetration enhancers also cause skin irritation, especially with prolonged exposure times. Some skin enhancing compounds, such as dimethyl formamide and dimethyl sulfoxide, may present potential toxicological complications.

Iontophoresis is a process which causes increased penetration of ionized compounds into the skin by use of an electrical gradient. Unfortunately, many of the drawbacks associated with transdermal administration also apply to iontophoresis. Additionally, delivery by iontophoresis is limited to compounds having readily ionizable groups.

Thus, it is desirable to provide a method for administering uncharged steroid hormones, such as the 17-hydroxy sterols, which allows delivery of therapeutically effective levels of drug, avoids excessive degradation of the active compound by the liver, avoids invasive routes of administration, and does not rely on the presence of potentially irritating or toxic skin permeation enhancing compounds.

SUMMARY OF THE INVENTION

The present invention provides compositions for use in improved transdermal transport of 17-hydroxy sterol compounds. In particular, the invention provides prodrugs of 17-hydroxy sterols which are modified at the 17-hydroxy position by covalent attachment of a chemical modifier. The chemical modifier provides the parent sterol with enhanced transport properties and is hydrolyzed under physiological conditions to release the active parent compound.

The prodrugs of the present invention are particularly useful for iontophoretically administering therapeutically active compounds which lack a formal charge or a readily ionizable functional group.

The chemical modifiers of the present invention are charged entities. The prodrug is a 17-hydroxy sterol/chemical modifier complex, more generally represented by the formula (sterol—O—)C(O)—R—N($R^1$)($R^2$)($R^3$)$^+$. The portion of the complex derived from the chemical modifier is indicated by "C(O)—R—N($R^1$) ($R^2$)($R^3$)$^+$".

In one embodiment of the invention, "—N($R^1$)($R^2$)($R^3$)$^+$" is a quaternary ammonium group and $R^1$, $R^2$, and $R^3$ are independently selected from the group consisting of lower alkyl, alkyl, aryl, arylalkyl, cycloalkyl, heteroalkyl, and heteroarylalkyl. Preferred lower alkyl groups include methyl, ethyl, n-propyl, and isopropyl. In an alternate embodiment, $R^1$ and $R^2$ together with the nitrogen to which they are attached form a substituted aromatic or aliphatic heterocycle and $R^3$ is lower alkyl.

"R" is a linking moiety, which links the 17-hydroxy oxygen of the parent sterol to the charged nitrogen atom. The linking moiety may possess an oxygen atom or a nitrogen atom connected to the carbonyl carbon, to provide a carbonate or carbamate linkage, respectively. Alternatively, the prodrug may contain an ester linkage, such as when a carbon atom of the linking moiety is connected to the carboxyl carbon. Additionally, the linking moiety may possess at least one internal carboxy, carbonate, amide or carbamate group.

More preferably, the parent sterol is modified for use in transdermal delivery by coupling at the 17-hydroxy position to a synthetic or naturally occurring amino acid or amino acid salt. Examples of linear or branched amino acid chemical modifiers for use in the invention include N,N-dimethylaminobutanoic acid, 4,-N,N,N-trimethylammonio-but-2-ene-oic acid, chloride salt, L-O-palmitoylcarnitine, 3-N,N,N-trimethylammoniopropanoic acid, bromide salt, and 4-N,N,N-trimethylammoniobutanoic acid, bromide salt.

In the present invention, the chemical modifier may include aliphatic nitrogen-containing heterocycles such as stachydrine and O-acetylbetonicine. Also useful as chemical modifiers are functionalized aromatic heterocycles such as nicotinic acid, trigonelline, picolinic acid and N-methylpicolinic acid. In one embodiment, $—R—N(R^1)(R^2)(R^3)^+$ is N-methylhordenine.

Also disclosed for use in modifying 17-hydroxy sterols for enhanced transdermal transport are negatively charged chemical modifiers. Examples of such chemical modifiers are typically compounds containing sulfate, sulfonate, phosphate, or phosphonate groups, which may be readily deprotonated to yield the corresponding salts. One such modified sterol according to the present invention is testosterone-17β-[taurine succinamide ester], triethylammonium salt.

In another aspect, also disclosed are 17-hydroxy sterol/chemical modifier complexes in which the sterol is attached to a charged chemical modifier through an acetal or ketal linkage.

In one embodiment of the invention, the 17-sterol compound is testosterone. In particular, testosterone is modified by attachment through the 17-hydroxy oxygen to a chemical modifier capable of providing enhanced iontophoretic transdermal uptake.

In another embodiment of the invention, the 17-sterol compound possesses a second derivatizable group, to which is attached a second chemical modifier. The second chemical modifier may be the same or different from the chemical modifier attached at the 17-hydroxy position.

Another aspect of the invention provides a method for enhancing the transdermal electrotransport of a 17-hydroxy sterol by derivatization at the 17-hydroxy position with a charged chemical modifier.

In another aspect, a method is provided for transdermally administering to a subject, a 17-hydroxy sterol. The sterol is iontophoretically administered as a sterol-chemical modifier complex having a physiologically cleavable bond connecting the sterol to the chemical modifier. After administering the complex, the bond is cleaved in vivo to release the sterol in its uncomplexed form.

These and other objects and features of the invention will become more fully apparent when the following detailed description is read in conjunction with the accompanying figures and examples.

BRIEF DESCRIPTION OF THE FIGURES

FIGS. 1A–F show the structure of testosterone, a 17-sterol for use in the present invention, as well as various prodrugs thereof. FIG. 1A indicates the structure of testosterone. FIG. 1B illustrates a testosterone/N-methylated amino acid complex in accordance with the invention, testosterone-17β-(N,N,N-trimethyl-β-alaninyl ester) bromide salt. The prodrug is a testosterone carboxy ester containing a trimethylammonio group in the 17-side chain. FIG. 1C is an exemplary carbonate ester prodrug of testosterone in which the chemical modifier additionally contains an internal carboxy group. FIG. 1D shows a testosterone-chemical modifier complex in which two chemical modifiers are attached to testosterone. The prodrug, testosterone-3-enol-17β-ol bis[4-N,N,N-trimethylammonio)butyrate], dibromide salt, contains charged modifiers at the 3 and 17 positions. FIG. 1E shows stachydrine testosteryl ester, a prodrug of testosterone with a charged nitrogen heterocycle-containing chemical modifier. FIG. 1F indicates another testosterone prodrug in accordance with the present invention, testosterone-17β-(N-methylpicolinate), hydrogen sulfate salt, in which testosterone is coupled to the N-methylated salt of picolinic acid.

The complex is prepared by treating testosterone with chloromethyl chloroformate to form the chloromethyl carbonate ester. The chloromethyl carbonate ester is converted to the corresponding iodo compound by treatment with sodium iodide, and then reacted with 6-bromohexanoic acid and DIEA to form testosterone-17β-(6-bromohexanoyl)oxymethyl carbonate. Treatment with sodium iodide to form the iodo carboxy adduct is followed by treatment with trimethylamine to form the desired prodrug.

Figure 3:
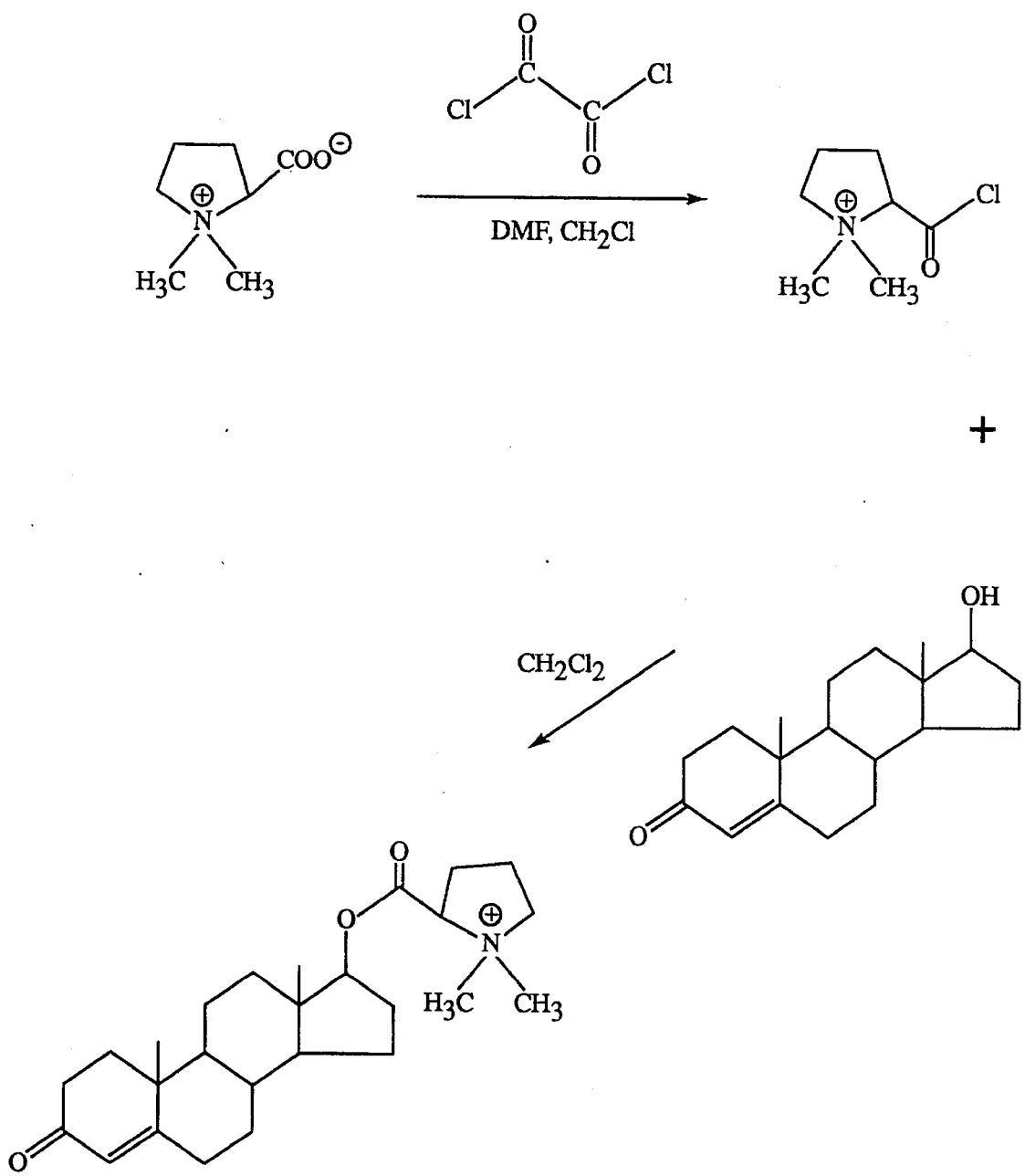

FIG. 3 illustrates an alternate synthetic methodology for forming a testosterone/chemical modifier complex. In this approach, stachydrine (2-carboxy-1,1-dimethylpyrrolidinium hydroxide, inner salt) is treated with oxalyl chloride in DMF to form the corresponding acid chloride. Testosterone is then mixed with the acid chloride to form the desired prodrug product.

Figure 4:
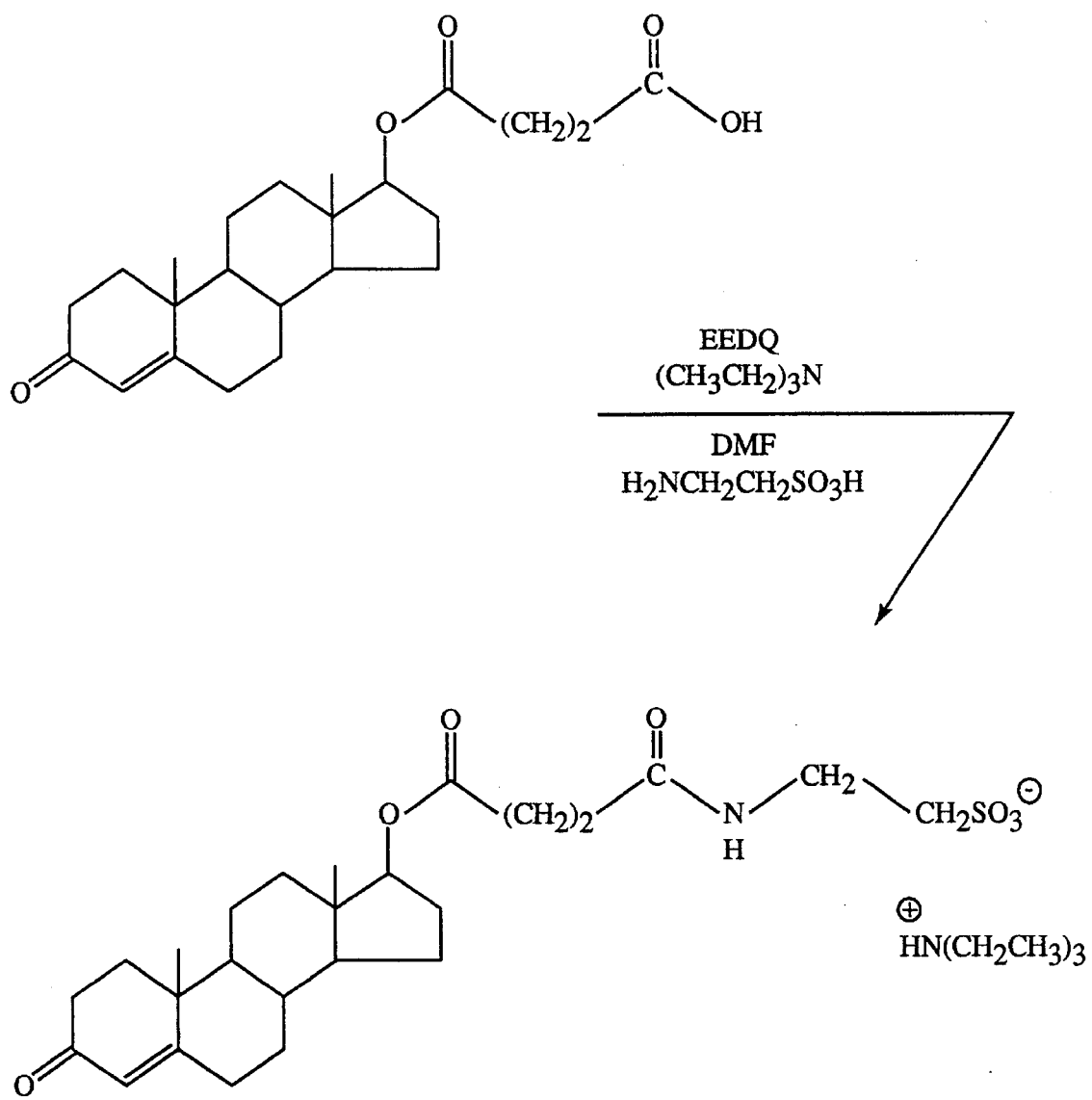

FIG. 4 illustrates one general approach for forming a negatively charged testosterone/chemical modifier complex. Testosterone-17β-succinate is treated with triethylamine and EEDQ (N-ethoxycarbonyl-2-ethoxy-1,2-dihydroquinoline), followed by treatment with taurine, to form the desired complex, testosterone-17β-[taurine succinamide ester], triethylammonium salt.

Figure 5:
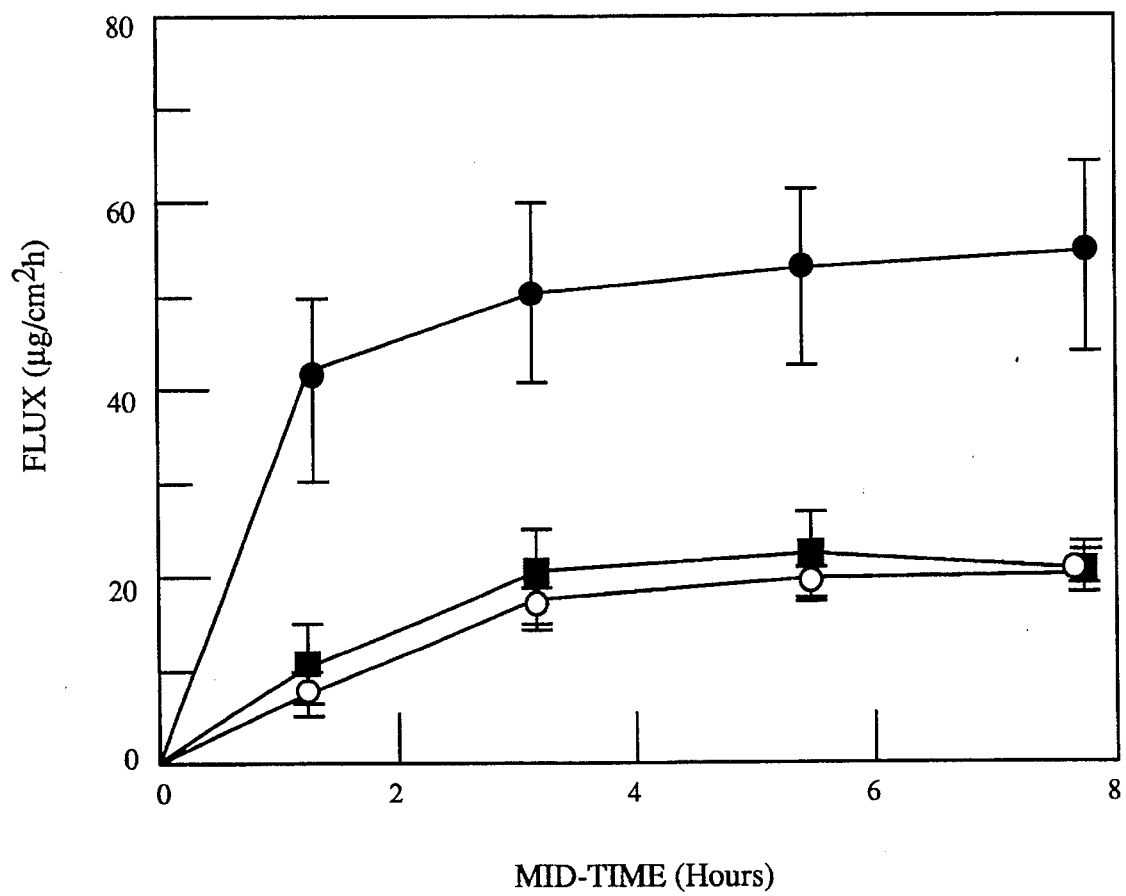

FIG. 5 illustrates the iontophoretically-induced flux rates of prodrugs of testosterone across human skin. Iontophoretic flux rates over time are plotted for testosterone-17β-stachydrine ester, chloride salt [2.9], (closed circles), testosterone-17β-(L-carnitine ethyl ester) carbonate, iodide salt [1.7] (solid squares), and testosterone-17β-choline carbonate, bromide salt [1.4] (open circles).

Figure 6:
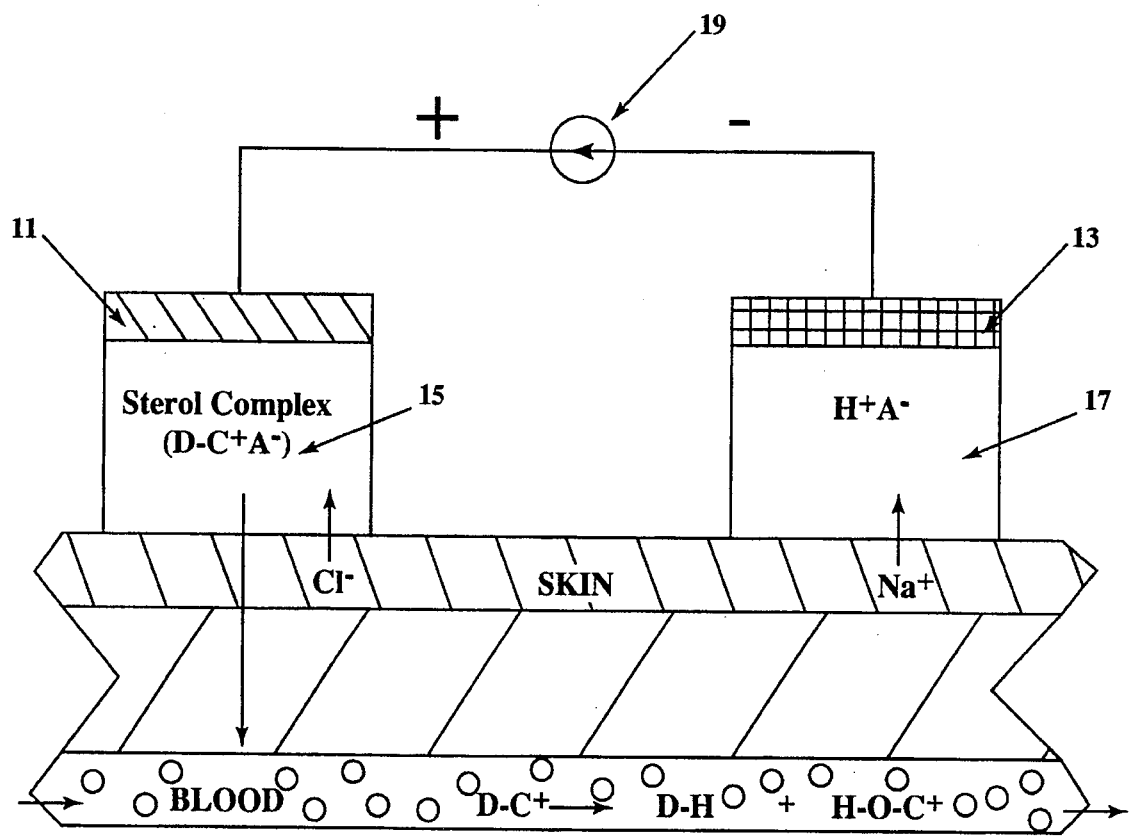

FIG. 6 is an exemplary iontophoretic delivery device for transdermal electrotransport of the testosterone prodrugs of the present invention.

DETAILED DESCRIPTION OF THE INVENTION

I. Definitions

The following terms, as used herein, have the meanings as indicated:

A "charged" moiety refers to any functional group or molecule possessing a formal charge, either by virtue of its inherent structure, as a result of covalently bonding to another atom, or as a result of pH conditions of the surrounding environment. The charge on the moiety may be either positive or negative.

A "17-hydroxy sterol" refers to a compound possessing the general steroid structure and having a hydroxy group attached to the 17-position of the ring. The compound may be naturally occurring or synthetic, and may contain additional functional groups within the steroid ring structure.

A "physiologically cleavable" bond is one that is cleaved or hydrolyzed in vivo, but may be cleaved by other in vitro agents as well. Hydrolysis may be chemical or enzymatic. For transdermally administered compounds containing physiologically cleavable bonds, hydrolysis may occur by the physiological processes in a cell, an organ, the skin, a membrane or elsewhere within the body of a patient.

"Transdermal delivery" refers to the transport of a substance across the epidermis and dermis, such as the skin or mucous membranes, so that the substance can enter the systemic circulation. Ideally, the substance will not reside in the skin for any extended period of time, but will reach and maintain therapeutic blood levels.

"Enhanced transdermal delivery" refers to the facilitation of transdermal delivery as a potential mode of substance administration. Enhanced transdermal delivery also refers to an absolute increase in the molar volume of a substance transported per unit time through a constant surface area as compared to that of a control substance. As used herein, enhanced transdermal delivery typically refers to improved transdermal transport as defined above, for a 17-hydroxy sterol/chemical modifier complex as compared to that of the unmodified, 17-hydroxy sterol.

"Iontophoresis" or iontophoretic delivery refers to the transport of ionizable or charged molecules into a tissue by the passage of an electric current through an electrolyte solution containing the molecules to be delivered.

As used herein, a "chemical modifier" refers to a charged molecule capable of covalently bonding to a pharmaceutical agent, another chemical modifier, or a spacer group. As designated herein, the portion of the 17-hydroxy sterol/chemical modifier complex considered as arising from at least one chemical modifier is represented as —C(O)—R—N($R^1$)($R^2$)($R^3$)$^+$, although any molecule giving rise to any portion of the above structure may be considered as a chemical modifier. The sterol/chemical modifier complex may be synthesized in any order, that is by first modifying the 17-hydroxy functionality on the parent sterol, followed by coupling to a chemical modifier, or, alternatively, suitably functionalizing the chemical modifier to form a reactive molecule capable of reacting with the sterol 17-hydroxyl. The term chemical modifier is meant to include both the charged molecule and its counterions, if any. Suitable anions include chloride, bromide, iodide, tetrafluoroborate, hydrogen sulfate, and other pharmaceutically acceptable salts. Suitable cations, for use with negatively charged complexes, include sodium, potassium, ammonium, mono, di- and tri-alkylammonium, and other pharmaceutically acceptable salts.

In the above formula, "R" is understood to be part of the chemical modifier and is a linking moiety which links the carbonyl carbon alpha to the sterol 17-oxygen to the quaternary nitrogen atom. The linking moiety may contain internal functional groups such as carboxy or carbamate. Additionally, "R" may possess a terminal heteroatom such as a nitrogen or oxygen connected to the carbonyl carbon of the chemical modifier to provide a carbonate or carbamate linkage. When considered together, R—N($R^1$)($R^2$)($R^3$)$^+$ of the above formula may represent part of an aliphatic or aromatic heterocycle.

"Amino Acid" refers to any compound containing both an amino group and a carboxylic acid group. The amino group may occur at the position adjacent to the carboxy function, such as in the α-amino acids, or at any location within the molecule. The amino acid may also contain additional functional groups, such as amino, thio, carboxyl, carboxamide, imidazole, etc. The amino acid may be synthetic or naturally occurring. As referred to herein, "amino acid" refers to both the parent compound and any N-methylated derivatives, such as the corresponding N-methylamino, N,N-dimethylamino, and N,N,N-trimethylammonio compounds, where applicable.

A "17-hydroxy sterol/chemical modifier complex" is a charged complex in which a chemical modifier, as described above, is covalently bonded to the 17-oxygen of a 17-hydroxy sterol. The term prodrug, as used herein, also refers to the sterol/chemical modifier complex, and may be used interchangeably therewith. The complex may be positively or negatively charged; for negatively charged complexes, such as when the chemical modifier or a portion of the chemical modifier is phosphate, the 17-sterol is not dexamethasone. The parent 17-hydroxy sterol may also contain additional chemical modifiers or functional groups.

II. The Pharmaceutical Agent

The present invention is particularly useful for the enhanced delivery of steroidal compounds. Steroid compounds for use in the present invention must contain at least one derivatizable functional group, capable of binding to a chemical modifier.

One such class of compounds are the 17-hydroxy sterols. Examples of 17-hydroxy sterols include various estrogenic compounds, such as estradiol, ethinyl estradiol, estriol, mestranol and quinestrol. Another class of compounds, the androgens, include various 17-hydroxy sterols, such as testosterone, methyltestosterone, stanolone, and stanozolol. The progestins include 17-hydroxy sterols such as hydroxyprogesterone and dimethisterone.

Steroidal estrogens may be naturally occurring, such as estradiol and estriol, or synthetic, such as ethyinyl estradiol, mestranol, and quinestrol. The estrogens have a number of physiologic effects and are required for normal maturation of the female. The estrogens also have a number of metabolic effects, such as the maintenance of the normal structure of the skin and blood vessels in women. Clinical uses of estrogenic compounds include contraception, treatment of primary hypogonadism, hormonal replacement therapy in postmenopausal women, and prevention of osteoporosis.

Progestins, such as 17α-hydroxyprogesterone, are most commonly used therapeutically for hormonal contraception. Progestins have also been employed in the treatment of dysmenorrhea, endometriosis, hirsutism, and bleeding disorders.

Androgenic compounds, such as testosterone (17β-hydroxyandrost-4-en-3-one), are required for sperm production and promote general growth of body tissues. One preferred compound for use in the present invention is testosterone, which in humans, is the most important androgen secreted by the testis. The primary clinical use of androgens is to replace or augment androgen secretion in hypogonadal men. Androgens may also be used to treat certain gynecologic disorders, such as to reduce breast engorgement during the postpartum period. Androgens may also be used to reduce protein loss after trauma, surgery, or prolonged immobilization, or in the treatment of anemia. Androgens may also be used in the treatment of osteoporosis or as metabolic growth stimulators in prepubertal boys.

Testosterone and its derivatives are particularly useful for modification for transdermal delivery by the methods of the present invention. Compounds which can best be modified for either active (i.e., iontophoretic) or passive transdermal transport are those which are therapeutically effective at low concentrations, e.g., the compound must have a potent pharmacological activity.

For many transdermal drug candidates, the amount of drug required transdermally to result in effective plasma concentrations of active agent is unknown and must be experimentally determined. Drug plasma levels depend on a number of factors such as half life and clearance values. As a general guideline, compounds for which the recommended daily dose (based on oral or parenteral routes of administration) is on the order of 50 milligrams or less are good candidates for transdermal delivery.

Testosterone and its derivatives are compounds which are therapeutically effective at fairly low doses. For instance, for use in replacement therapy, methyltestosterone has a recommended daily dose of 25–50 mg when administered orally and 2–10 mg when administered buccally. Similarly, fluoxymesterone has a recommended oral daily dosage of 2–10 mg, while testosterone propionate is administered at 5–20 mg per day buccally. Compounds for use in the present invention are those which preferably maintain or even augment their therapeutic activity upon binding to one or more chemical modifiers.

III. Chemical Modifiers

The chemical modifiers of the present invention are charged molecules or functional groups capable of attachment to a pharmaceutical agent or agents for the purpose of providing the agent with enhanced percutaneous delivery properties. Additionally, attachment of a modifier may result in additional, and ideally beneficial, changes to the properties of the agent to be delivered, such as altered biological half life, shorter lag times preceding the attainment of steady state blood plasma concentrations, increased stability in vitro, reduced toxicity, and the like. The chemical modifiers are most appropriate for use in modifying agents intended for iontophoretic administration.

The chemical modifier may be positively or negatively charged. Most typically, positively charged chemical modifiers contain an ionizable nitrogen atom, such as in amino-containing compounds. Alternatively, the chemical modifier may impart a negative charge to the resulting complex, typically by virtue of a sulfate, sulfonate, phosphonate or phosphate group.

For chemical modifiers possessing a formal charge, the accompanying counterion is also considered to be part of the chemical modifier. Preferably, the counterions for both the chemical modifier and the resulting modified sterol complex result in pharmaceutically acceptable salts, containing anions such as chloride, bromide, iodide, acetate, methanesulfonate, succinate, and the like.

Preferred chemical modifiers are those which are non-toxic or are rapidly degraded to non-toxic components upon cleavage from the parent drug. Additionally, the chemical modifier, when covalently linked to the parent compound, should not adversely impact the toxicity of the parent drug.

Ideally, and in certain instances, the chemical modifier will possess therapeutic activity of its own, in addition to modifying the transport properties of the active agent. For example, the amino acid carnitine (3-carboxy-2-hydroxy-N,N,N-trimethyl-1-propanaminium hydroxide, inner salt) is used therapeutically as an antihyperlipoproteinemic, and the hydrochloride is used as a gastric and pancreatic secretion stimulant.

The chemical modifier is attached to the parent drug by a physiologically cleavable bond, which when hydrolyzed, results in the in vivo release of the active drug. Ideally, the pharmaceutical agent-chemical modifier complex is stable in vitro for extended periods of time. Further, the drug-chemical modifier linkage should be stable upon application of an electric current, such as during iontophoretic delivery. In some instances, the chemical modifier is a naturally occurring compound.

Preferably, the modifier is attached to the 17-hydroxy oxygen of a sterol. Chemical modifiers containing the following reactive groups are appropriate for reacting with the hydroxy oxygen of a sterol and include carboxy, hydroxy, amino, sulfate, phosphate, keto and aldehyde.

Preferred chemical modifiers for use in the present invention are those which can be considered to give rise to any portion of the following formula —C(O)—R—N($R^1$)($R^2$)($R^3$)$^+$. "—R—", considered to be part of the chemical modifier, is a linking moiety which links the carbonyl carbon alpha to the sterol 17-oxygen to the quaternary nitrogen atom. Additionally, "R" may possess a terminal heteroatom such as a nitrogen or oxygen connected to the carbonyl carbon of the chemical modifier to provide a carbonate or carbamate linkage. When considered together, R—N($R^1$)($R^2$)($R^3$)$^+$ of the above formula may represent part of an aliphatic or aromatic heterocycle.

The "R" portion of the chemical modifier may optionally contain one or more internal functional groups, such as carboxy, carbonate, carbamate, alkenyl, alkynyl, keto, thio, mercapto, and the like. Optional functional groups internally located in the "R" linking moiety should be fairly inert in vitro and may or may not impart additional charge to the chemical modifier.

As indicated above, preferred chemical modifiers are those containing a charged nitrogen atom such as quaternary ammonium compounds. Exemplary chemical modifiers are those containing quaternary lower alkyl functions, such as trimethylammonium. Quaternary ammonium groups may be present in the chemical modifier prior to attachment to the sterol, or alternatively, the chemical modifier amino group can be alkylated subsequent to attachment of the "pre"-chemical modifier to the agent.

One preferred group of chemical modifiers are the amino acids or quaternary amino acid salts. The amino acids may be naturally occurring or synthetic, or may be derivatives of naturally occurring compounds. The carboxy portion of the molecule provides a site of attachment to the parent sterol, while the amino group provides the charged portion of the chemical modifier.

Alternatively, the amino group may be used to bind to the sterol by means of a carbamate linkage. In this embodiment, the sterol is first transformed to the corresponding chloroformate by reaction with, for instance, phosgene, and then coupled to the amino group of the chemical modifier. In the above embodiment, the charged portion of the chemical modifier is provided by the carboxylate anion of the carboxylic acid.

Amino acids for use in the invention include compounds such as carnitine, lysine (2,6-diaminohexanoic acid), ornithine (2,5-diaminopentanoic acid), and betaine (1-carboxy-N,N,N-trimethylmethanaminium hydroxide inner salt). Simple straight chain amino acids, and their corresponding quaternary ammonium salts, may also be used. Such compounds include 3-N,N-dimethylaminopropanoic acid and its trimethyl ammonium salt, 4-N,N-dimethylaminobutanoic acid, and similar homologous compounds.

Carnitine, a hydroxy-substituted trimethylammonium compound, is a non-toxic, naturally-occurring amino acid. Carnitine contains one chiral center and may be used in either its racemic or optically active (D-, or L-) form. The 2-hydroxy function of carnitine may also be converted to another functional group to provide derivatives of carnitine for use in the present invention. As discussed above, L-carnitine is therapeutically useful in the treatment of hyperlipoproteinemia, while the D,L-form is active as a gastric and pancreatic secretion stimulant.

Lysine may also be used as a chemical modifier. Lysine possesses two amino groups, and either or both may be alkylated (either partially or exhaustively) for use in the present invention. One of the amino functions of lysine may also be further derivatized to add both mass and alternate functionality to the chemical modifier. For instance, the amino group could readily be converted to an amide by reaction with a carboxy-containing reagent.

Heterocyclic amino acids and their corresponding quaternary ammonium salts are also useful in the present invention. Examples of aliphatic N-containing heterocycles for use as chemical modifiers in the present invention include betonicine, its stereoisomer, turicine, and stachydrine.

Betonicine (trans-2-carboxy-4-hydroxy-1,1,-dimethylpyrrolidinium hydroxide, inner salt) and its cis isomer, turicine, are naturally occurring substituted pyrrolidines. The carboxy group provides a site of attachment to the parent sterol compound, while the hydroxy group may be utilized, if desired, for further derivatization. For instance, betonicine may be converted to an ester derivative, such as O-acetylbetonicine, by reaction with acetyl chloride.

Stachydrine (2-carboxy-1,1-dimethylpyrrolidinium hydroxide inner salt) is a naturally occurring carboxy pyrrolidine compound, similar in structure to betonicine, but lacking a hydroxy substituent.

Further examples of chemical modifiers include aromatic heterocycle-containing carboxylic acids. The aromatic heterocycle may be nitrogen containing or may possess a nitrogen-containing substituent. The nitrogen atom may be attached directly to the aromatic ring, or separated by one or more carbon atoms.

Examples of such compounds include nicotinic acid, trigonelline, picolinic acid, and N-methylpicolinic acid. Nicotinic acid (3-pyridinecarboxylic acid) and picolinic acid (2-pyridinecarboxylic acid) are structural isomers, differing only in the relative positions of the carboxy groups on the pyridine ring.

Nicotinic acid or niacin, is a naturally-occurring compound. Minute amounts of nicotinic acid exist in all living cells, and nicotinic acid functions therapeutically as a vitamin. Both nicotinic acid and its N-methylated derivative, trigonelline, may be used as chemical modifiers. Trigonelline is also naturally-occurring, and is found in coffee beans and in the seeds of many plants. Further examples of chemical modifiers include the aminoalcohols. In utilizing this class of compounds, the amino group provides the charged functionality, while the hydroxy group is utilized to couple to the modified parent sterol. One such compound is hordenine, 4-[2-(dimethylamino) ethyl]phenol, and its N-methylated analogue.

Although considered as one entity when attached to the sterol, the chemical modifier, as defined in the resulting complex, may be introduced into the drug by a number of synthetic transformations to construct the ultimate modifier group, or may be attached directly to the sterol. Synthetic transformations may also be carried out at the sterol 17-oxygen position to provide a reactive center suitable for coupling to a chemical modifier.

IV. The Linkage

The prodrugs of the present invention possess a physiologically cleavable bond between the active agent and the chemical modifier. For compositions containing a 17-hydroxy sterol\chemical modifier complex, the complex contains a physiologically cleavable bond connecting the sterol to the chemical modifier. The bond is preferably stable in vitro, but readily hydrolyzed in vivo to release the active form of the parent drug and the chemical modifier.

Appropriate linkages for attaching chemical modifiers to hydroxy-containing compounds include but are not limited to ester, carbonate ester, carbamate, sulfate, phosphate, acyloxyalkyl ether, acetal, and ketal.

The chemical modifier may contain other internal bonds which are cleaved under physiological conditions, so that the chemical modifier is further degraded upon release from the active agent. Preferably, the chemical modifier, when present in the subject in its free or released form, and in appropriately administered amounts, should be non-toxic. Additionally, any further in vivo degradation products of the chemical modifier should be non-toxic, as well.

For use in iontophoresis, the complex should possess a physiologically cleavable bond which is stable upon application of an electric current. For instance, for an active agent\chemical modifier complex intended for iontophoretic administration, the complex should maintain its integrity upon dissolution in an appropriate delivery vehicle, placement in the iontophoretic device, and upon application of electric current.

For complexes in which the active agent is attached to more than one chemical modifier, the additional chemical modifier is also attached to the active agent by means of a physiologically cleavable bond. The chemical modifiers may be hydrolyzed in vivo from the parent compound at the same or different rates, depending on the type of bonds linking the modifiers to the active agent (i.e., carboxy ester, amide, carbamate, carbonate ester).

Preferred linkages for use in the present invention include carboxy and carbonate esters. Also preferred are carbamate linkages. The preferred linkage is indicated in the 17-hydroxy sterol/chemical modifier complex formula as "(sterol—O—)C(O)—R—", where for complexes containing a carbonate ester, the "R" linking moiety contains an oxygen atom connected to the carbonyl carbon indicated in the above formula. For complexes possessing a carbamate linkage, the "R" linking moiety contains a nitrogen atom connected to the carbonyl carbon indicated in the above formula.

V. Preparation of the Pharmaceutical Agent/Chemical Modifier Complex

Typically, the methods described below will be applied to steroid compounds possessing at least one chemical group suitable for attaching to a chemical modifier. More preferably, the methods described will be applied to sterols.

A. Sterol-Chemical Modifier Complexes Possessing a Physiologically Cleavable Ester Bond In one embodiment of the present invention, the sterol is attached to the chemical modifier by means of a carboxy ester linkage. Depending on the structure of the active agent and the intended prodrug product, the order of the coupling reactions may or may not matter. In cases in which the active agent possesses more than one derivatizable group, some functional groups may require protecting groups to prevent unwanted transformations. This will depend on the nature of the active agent, the reagents utilized for transformations, and the like, and will be obvious to one of ordinary skill in the art.

For example, for sterol compounds containing more than one reactive hydroxy moiety, protection of additional hydroxyl groups may be required by one of the methods commonly known in the art. In this case, and depending on the desired products, variations in synthetic methodology may be employed which take into account the differences in activity of the hydroxyl groups, the proposed position for attachment of the chemical modifier, and the like. Commonly used groups for protection of alcohols include trityl or one of the methoxytrityl protecting groups, isobutyloxycarbonyl, or silyl ethers, such as trimethylsilyl ether.

For chemical modifiers containing reactive amino groups, any of a number of amino protecting groups may be used, such as carbobenzoxy (CBZ), tert-butoxycarbonyl (t-BOC), trityl derivatives such as trityl (Tr), dimethoxytrityl (DMTr) and the like. Other protecting groups, such as cyclic diacyl groups or nitrophenylsulfenyl (Nps) may also provide suitable reagents for protecting amino functions.

A suitable protecting group for use in the present invention is one which is easy to introduce into the molecule, protects the desired functional group under reaction conditions effective to introduce the chemical modifier, and is removable under conditions (either acidic or basic) which leave the physiologically cleavable bond between the sterol and the chemical modifier intact.

FIGS. 1B, 1D, 1E, and 1F show exemplary complexes possessing ester bonds connecting testosterone to the chemical modifier.

In one typical synthetic approach, such as that utilized to form the prodrug shown in FIG. 1B, 17-testosteryl(3-N,N,N-trimethylammonio)propanoate, an amino acid provides the chemical modifier for conversion of testosterone to a prodrug. Similar techniques were utilized to form the testerone-chemical modifier complexes shown in FIGS. 1E and 1F.

In this approach, the chemical modifier, 4-(dimethylamino)butyric acid hydrogen chloride, is activated prior to coupling to testosterone by conversion to the corresponding acid chloride. A number of chlorinating reagents may be used, such as oxalyl chloride, phosphorus trichloride, thionyl chloride or the like. Upon formation of the acyl chloride, the activated amino acid is then reacted with testosterone, or any suitable sterol, in a dry solvent, such as methylene chloride, to provide the sterol-amino acid adduct.

The resulting complex may be further N-alkylated, if desired, by reaction with an appropriate alkylating reagent. Typically, tertiary amines are reacted with alkyl halides, much as bromomethane, or iodomethane, to form the corresponding N-methylated ammonium salts. Oxonium salts, such as trimethyl oxonium tetrafluoroborate, and triethyl oxonium tetrafluoroborate, may also be used, depending on the anion desired and the atom to be alkylated.

In some reactions, a functionalized amino acid may be used as the chemical modifier, such as 4-hydroxyproline or the corresponding N-alkylated compound. In this instance, the 4-hydroxy group provides an additional site for derivatizing the amino acid modifier, if desired. For instance, the hydroxy function may be reacted with an acyl chloride, such as acetyl chloride or palmitoyl chloride, to form the corresponding ester derivative, prior to coupling to the active agent. Alternatively, one may carry out a dehydration reaction on a hydroxy-containing compound, such as carnitine, to produce the corresponding alkene. For representative transformations of hydroxy groups, see for example, Wade (1984).

The use of chemical modifiers containing readily derivatizable groups allows flexibility in modifying the desired properties of the prodrug, such as serum halflife, lipophilicity and the like. Chemical modifiers possessing multiple functional groups may also be attached to more than one pharmacological agent molecule.

In an alternate approach, the sterol-chemical modifier complex may be constructed by sequential reactions at the sterol hydroxy group. For example, the ester linkage may be introduced by reaction of testosterone with a haloalkyl acid chloride, such as bromoacetyl chloride or 3-bromopropionyl chloride, to produce the corresponding bromoalkylcarboxy testosterone compound. The charged portion of the chemical modifier is then introduced into the molecule by reaction of the bromo group with an amine, such as trimethyl amine, to form the corresponding quaternary ammonium salt. If conversion of the accompanying counterion is desired, reaction with an appropriate anion exchange resin may be utilized.

Testosterone also possesses a keto group at the 3-ring position which may be used for introducing additional functionality into the parent sterol. In one embodiment of the present invention, a second chemical modifier is introduced into testosterone by conversion of the 3-keto group.

A number of possible transformations of the testosterone keto group may be utilized. One possible approach for forming a bis-chemical modifier complex of testosterone is as follows. The 17-hydroxy function is first converted to the corresponding bromoalkylcarboxy group by reaction with an equivalent of 4-bromobutanoic anhydride, followed by reaction of the isolated testosterone adduct with additional anhydride reagent in the presence of p-toluenefulfonic acid. The resulting 3,17-di-ester adduct may then be further derivatized at the reactive bromo groups or treated with an appropriate amine to introduce the charged portion of the chemical modifier, in accordance with the invention. Preparation of such a symmetrical bis adduct, testosterone-3-enol-17β-ol bis[4-(N,N,N-trimethylammonio)butyrate], dibromide salt, [4.3], is described in Example 13.

The above describes the preparation of a symmetrical bis-chemical modifier complex of testosterone, however, by selection of appropriate reagents, bis adducts having different functional groups at the 3- and 17-positions may be used as well. Preparation of an exemplary unsymmetrical bis-chemical modifier complex of testosterone, testosterone-3-enol, 17β-ol 3-(N,N,N-trimethyl-β-alanine ester) 17-(choline carbonate), dibromide salt, [4.4], is described in Example 12.

Figure 2A:
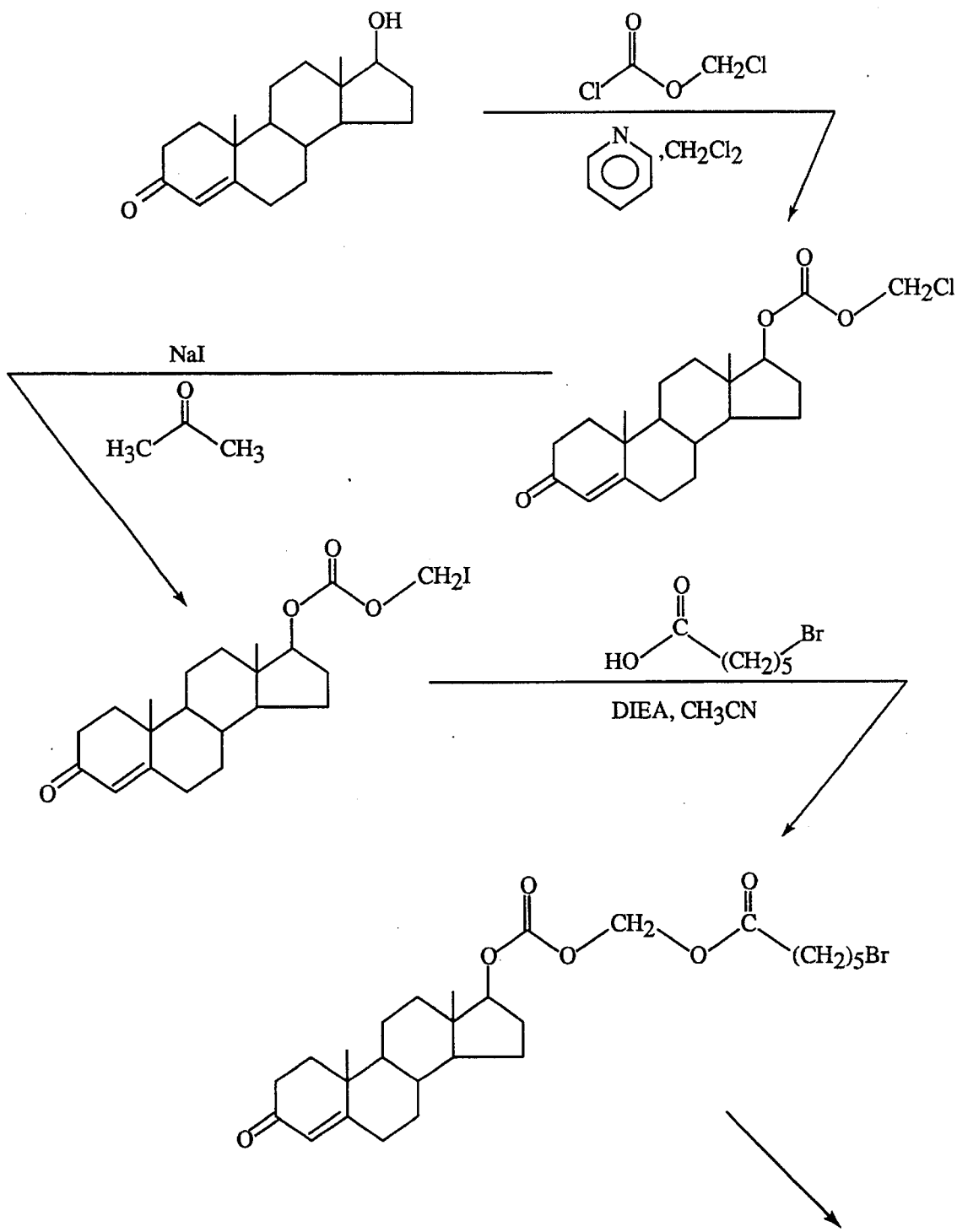
FIG. 2 illustrates one general synthetic approach for forming a prodrug of testosterone. In the synthetic method shown, a portion of the chemical modifier is first attached to the testosterone skeleton, and then further derivatized to form the final prodrug.
Figure 2B:
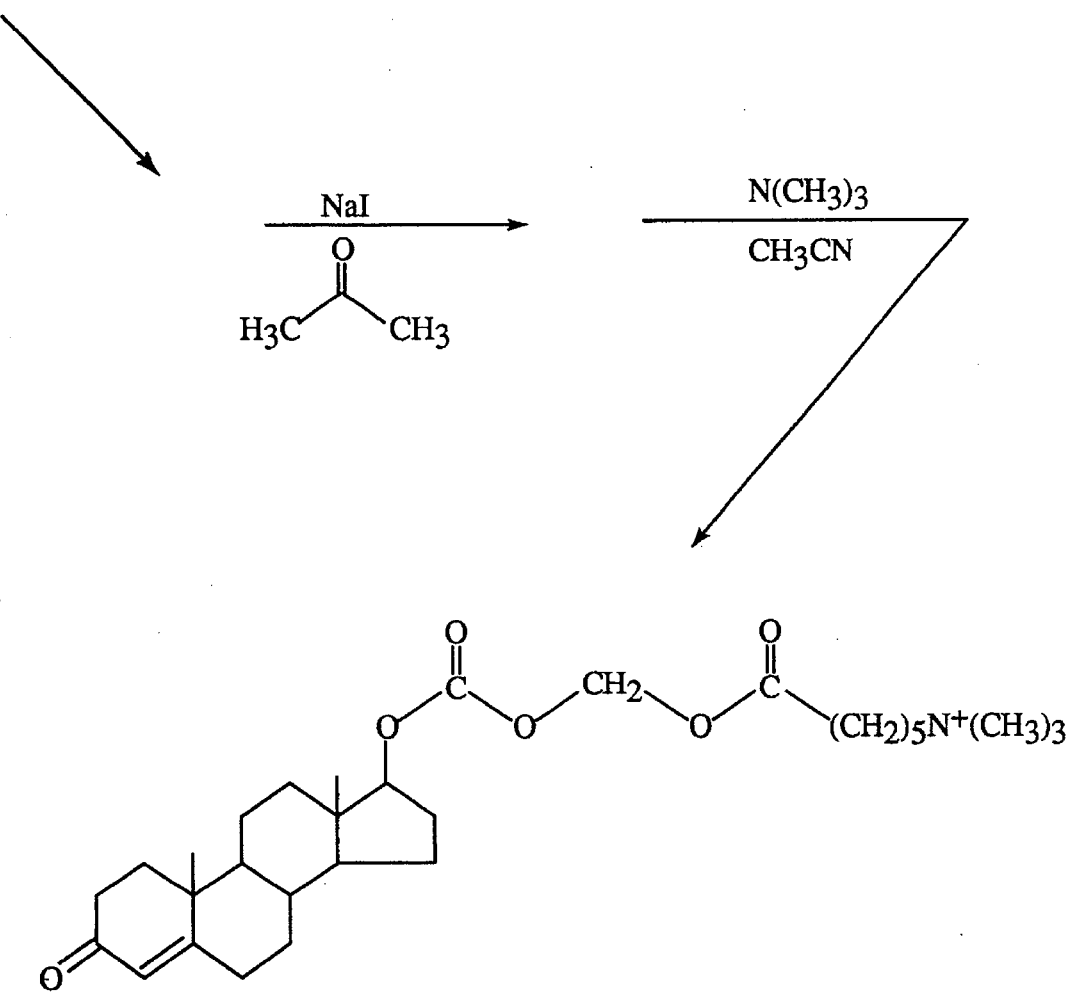

B. Sterol-Chemical Modifier Complexes Possessing a Physiologically Cleavable Carbonate Bond In another embodiment of the present invention, the sterol is attached to the chemical modifier by means of a physiologically cleavable carbonate ester linkage, as illustrated in FIGS. 1C and 2.

In one typical approach, a sterol such as testosterone is treated with a reagent such as 2-bromoethyl chloroformate.

The chloroformate portion of the reactant transforms the sterol hydroxy group to the corresponding carbonate, while the bromo atom provides a site for further transformations. For instance, the carboxy testosterone adduct may be treated with a suitable amine for conversion to the corresponding charged quaternary ammonium group.

Alternatively, a second chemical modifier may be introduced at the 3-keto position of testosterone by reaction with a suitable anhydride reagent, such as β-bromopropionic anhydride, in the presence of p-toluene sulfonic acid. The resulting bis adduct will possess a carbonate linkage at the 17-ring position, and an ester linkage at the 3-position, which may be further derivatized as in the preceding examples, and as described in section V(A) above.

The desired carbonate-containing chemical modifier may also be constructed by sequential reactions at the 17-sterol position. In one general approach, testosterone is treated with phosgene to form the corresponding testosterone chloroformate. Upon formation of the chloroformate adduct, reaction with any of a number of hydroxy-containing reagents will be effective to introduce the desired carbonate linkage into the testosterone prodrug skeleton.

For example, reaction of testosterone chloroformate with hordenine in the presence of DIEA results in formation of the corresponding testosterylcarbonate hordenine complex, testosterone-17β-(L-carnitine ethyl ester) carbonate, bromide salt [4.1], as described in Example 7. Similarly, testosterone chloroformate may be treated with a functionalized aminoalcohol such as ethyl(4-N,N-dimethylamino-2-hydroxybutanoate) to form the resulting testosterone chemical modifier complex, testosterone-17β-(L-carnitine ethyl ester) carbonate, iodide salt [1.7]. The hydroxy group is utilized to form the desired testosterone carbonate bond, while the amino group provides the chemical modifier with the charged portion. The ester group provides additional functionality to the chemical modifier, which may be used as a site for further transformations, or to modify the properties of the resultant prodrug, such as melting point, solubility, lipophilicy, charge, serum halflife, and the like.

As discussed in section IV, the methods of preparation will vary according to the type of bond desired for linking the chemical modifier to the sterol. For instance, if a carbamate linkage is desired, one could readily modify the methods outlined above by treating testosterone chloroformate with a diamino chemical modifier.

VI. Compositions of the Sterol/Chemical Modifier Complex

Once prepared, the testosterone prodrugs of the present invention may be utilized for administration by one of a number of potential routes, including enteral and parenteral. One preferred route of administration for the compositions of the present invention is percutaneous or transdermal administration. In a preferred embodiment of the invention, the 17-sterol/chemical modifier complex is for use in iontophoretic delivery.

For use in iontophoretic delivery, the 17-sterol prodrugs of the present invention provide complexes having a charge-to-mass ratio that allows percutaneous administration of the prodrug in therapeutically effective amounts. Typically, the charge-to-mass ratio of a sterol/chemical modifier complex will be equal to or exceed one charge per 5000 daltons. Preferably, the charge-to-mass ratio will be equal to or exceed one charge per 2500 daltons. Most preferably, the charge-to-mass ratio will be equal to or exceed one charge per 1000 daltons.

The compositions of the present invention may include the sterol prodrug admixed with an acceptable physiological carrier, such as water, aqueous alcohols, glycols such as propylene glycol, and the like. The composition may also contain other materials such as dyes, pigments, inert fillers, skin permeation enhancers, excipients, or other conventional products of pharmaceutical products or transdermal therapeutic systems known in the art.

VII. In Vitro Testing of the 17-Sterol/Chemical Modifier Complex

The hydrolytic activity of the sterol prodrug may be evaluated by studies of the chemical or enzymatic conversion of the prodrug to the unmodified parent compound, as described in Example 26.

Generally, the sterol/chemical modifier complex is dissolved in a minimum amount of a suitable solvent, such as ethanol, and the resulting solution is added to a sample of human serum. Following incubation, aliquots are then removed at various time points and analyzed to determine the extent of hydrolysis. Table I herein lists the representative serum half-lives of a number of testosterone prodrugs according to the present invention.

The rates of conversion are readily determined, for example by spectrophotometric methods or by gas-liquid or high performance liquid chromatography. Half-lives and other kinetic parameters may then be calculated using standard techniques.

The electrotransport behavior of the charged or modified complex in comparison with the parent sterol may be preliminarily assessed or screened using the above analytical techniques along with gel or capillary electrophoresis. Typically, if a complex exhibits a faster mobility during electrophoresis than the parent sterol, then that prodrug warrants further study as a candidate for improved iontophoretic transdermal delivery.

Other in vitro methods for assessing the feasibility of transdermal delivery include the determination of skin permeation rates. Typically, these experiments are carried out using a variety of skin diffusion cells and experimental protocols (Banga, 1988). Skin permeation data for various prodrugs of testosterone is provided in Tables 3 and 4 herein.

In conducting skin flux experiments, a number of variables are typically monitored such as temperature, type of skin used, skin thickness and skin surface covering, agitation of the donor/receiver phases, and the like.

One common technique employs flow-through diffusion cells, although static diffusion cells may be used as well. Typically, these cells have an active area of approximately 1 $cm^2$ and a receiving volume of 2–3 ml, and the skin sample is retained in a junction between the two cells. The skin is oriented at right angles to the diffusion cells.

The receptor compartment should be of sufficient volume to maintain infinite sink conditions. The receptor fluid, typically phosphate-buffered isotonic saline, is pumped into and through the cells by a peristaltic pump, and samples are collected at various time points and analyzed for content.

The donor compartment may contain a solution of the sterol prodrug dissolved in an appropriate solvent system, or, alternatively, contained within a transdermal device, such as a patch. The prodrug-containing medium is then placed directly on the stratum corneum, and the amount of drug permeating across the skin calculated. The above techniques may also be used to evaluate the transdermal electrotransport of a prodrug in vitro by applying an electric current through a solution containing the agent to be delivered.

In vitro electrotransport of testosterone/chemical modifier complexes across hairless mouse skin was evaluated as described in Example 28. The experiments were conducted using modified Valia-Chien cells having 1.0 ml donor and 2.5 ml receptor cells. Anodic transport was carried out using a silver wire-based salt bridge in the donor compartment and a silver chloride cathode in the receptor. Cathodic transport was effected by reversing the electrode configuration. The cells were connected in series and a constant current and temperature were supplied to each cell.

After a predetermined period of time (6 h), aliquots were removed from the receiver phase for immediate analysis by HPLC to determine cumulative flux. As shown in Table 3, sixteen of the sterol/chemical modifier complexes, or nearly 70%, exhibited enhanced electrotransport in comparison to the unmodified parent sterol, testosterone. Further, four complexes, testosterone-17β-choline carbonate, bromide salt [1.4], testosterone-17β-(N,N,N-trimethyl-β-alaninyl ester), bromide salt [2.5], testosterone-17β-[(4-N,N,N-trimethylammonio)crotonate] chloride salt [3.8], and testosterone-17β-(L-carnitine ethyl ester) carbonate, bromide salt [4.1], exhibited a nearly 10-fold enhancement or greater in in vitro electrotransport skin flux when compared to the unmodified sterol compound, testosterone.

Another useful factor for in vitro assessment of skin permeability of a target drug or drug complex is steady state flux. Typically, when performing a kinetic analysis of the skin-penetrating ability of a target compound through a membrane, such as skin, such an analysis includes an assessment of the lag time and the steady state flux or permeation rate. The ideal membrane for such determinations is human skin.

Steady state flux across human skin was determined for three distinct testosterone/chemical modifier complexes, as shown in FIG. 5 and in Table 4. In FIG. 5, iontophoretic flux rates over time are plotted for testosterone-17β-stachydrine ester, chloride salt [2.9], (closed circles), testosterone-17β-(L-carnitine ethyl ester) carbonate, iodide salt [1.7] (solid squares), and testosterone-17β-choline carbonate, bromide salt [1.4] (open circles). As shown in Table 4, the former compound, testosterone-17β-stachydrine ester, chloride salt [2.9], (closed circles) attained a steady state flux of 184 nmol/cm$^2$/h, which was greater than twice that of either of the other two testosterone/chemical modifier complexes. Steady state flux values in FIG. 5 are expressed as testosterone equivalents in units of μg/cm$^2$h.

As discussed above, the chemical modifier, when present in the subject in its free or released form, and in appropriately administered amounts, should preferably be non-toxic. Additionally, any further in vivo degradation products of the chemical modifier should be non-toxic, as well. Table 2 provides in vitro relative cytotoxicity data for a number of testosterone/chemical modifier complexes, prepared in accordance with the invention. The cytotoxicity assessment was carried out by examining the viability of human dermal fibroblasts in the presence of a number of testosterone/chemical modifier complexes in accordance with the present invention. Details of the experimental protocol are summarized in Example 27.

VIII Administration of the Sterol-Chemical Modifier Complex

As mentioned above, the 17-hydroxy sterol prodrugs of the present invention may be delivered transdermally. Transdermal delivery systems have the potential for providing a subject with sustained plasma concentrations of drug over a prolonged period of time. Ideally, the prodrugs of the present invention will provide enhanced transdermal uptake over that of the unmodified parent compound. In a preferred embodiment, the prodrugs are administered transdermally by iontophoresis. In one aspect, the invention also provides a method of treating hypogonadism by enhanced iontophoretic delivery of a testosterone prodrug.

Preferred 17-hydroxy sterols for use in the present invention are those which are therapeutically effective when transdermally administered at doses less than about 50 mg per day. The amount of any given drug to be administered will also vary depending upon its intended clinical use. For instance, testosterone may be used clinically i) to augment endogenous androgen secretion in men, ii) to treat certain gynocological disorders in women, iii) in combination with estrogen as replacement therapy for post-menopausal women, iv) to treat anemia, v) to treat osteoporosis, or vi) as a metabolic stimulator to stimulate growth in prepubertal boys. As is evident from its variety of uses, the dosage of testosterone-chemical modifier complex to be administered transdermally will be adjusted according to its intended therapeutic application, with preferred dosages ranging from about 2–50 milligrams per day.

Percutaneous delivery is accomplished by exposing a source of the prodrug complex to a patient's skin for a prolonged period of time. Skin sites for transdermal administration include anatomic regions such as the forearm, abdomen, chest, back, buttock, and the like.

Typically, the complex is incorporated into a matrix or reservoir from which it is released onto a patient's skin. Transdermal delivery systems containing the sterol\chemical modifier compositions of the present invention may include many of the following components.

Ideally, the choice of transdermal delivery system and components, as well as the drug complex to be delivered, will not cause an adverse cutaneous response. If an adverse skin reaction, such as irritancy, contact allergy, or a photoirritant reaction, does occur, its effects on the patient should be minimal. Upon selection of a target sterol/chemical modifier complex to be delivered, assessment of skin irritancy and contact allergy is carried out by methods commonly employed in the art (Steinberg, 1984; Anderson, 1987).

A. Passive Transdermal Drug Delivery Devices

A variety of transdermal patch types will find use in delivery of the 17-sterol/chemical modifier complexes of the present invention. For example, in one embodiment of the invention, the 17-sterol/chemical modifier complex is contained within a simple adhesive patch. In this formulation, the 17-sterol/chemical modifier complex is admixed with an adhesive polymer to provide a prodrug adhesive layer, which is cast directly onto an appropriate backing material. The adhesive matrix may also contain small quantities of skin permeation enhancing compounds. A release liner may optionally be affixed to the adhesive to complete the system.

Adhesive polymers for use in preparing transdermal patches typically belong to one of the following classes of polymers: acrylic-based polymers, silicones, and polyisobutylenes. In some embodiments, a hydrogel may be used. The choice of adhesive will depend on a number of factors including the structure of the prodrug to be administered, the target skin flux value, and the presence of other patch components which may affect certain properties of the adhesive, such as sheer strength and tack.

The backing layer should be impermeable to the prodrug and any added enhancers; typically, the backing is also impermeable to water (that is to say, it is occlusive). Typical backing layers for use in the invention include materials supplied by 3M and Dow Corning, such as polyester-polyethylene coextruded films, and polyurethane or polyethylene based materials, which can absorb perspiration.

The peel strip or release liner prevents the loss of prodrug that has migrated into the adhesive layer and protects the patch against contamination. Materials for use as release liners include polyesters, foil, mylar, and other metallized laminates.

Ideally, transdermal delivery systems for use in the present invention will range in size from 5–50 cm$^2$ in active releasing area. The ultimate configuration of the transdermal system will vary depending on a number of factors, including the prodrug to be delivered, its therapeutically effective dose, clinical use, desired length of time of patch wear, and the like.

In a matrix patch configuration, the prodrug is dispersed in a polymer medium. In some instances, the polymer provides a rate-limiting medium for release of the active agent. In an adhesive matrix type patch, the prodrug is dispersed in an adhesive polymer which attaches directly to the skin.

Alternatively, a monolithic or matrix type patch may be utilized to administer the 17-sterol prodrugs of the present invention. This patch configuration includes a backing layer, a drug-containing matrix layer, a separate adhesive layer, and an optional release liner. In this embodiment of the invention, the prodrug is dispersed in a rate-controlling polymer. In some instances, the patch may also contain an additional membrane layer interposed between the drug-containing polymer and the adhesive layer.

One such patch for delivering the 17-sterol\chemical modifier complexes of the present invention is a polyurethane patch. In this embodiment, the sterol prodrug is dispersed in a polyurethane prepolymer matrix. Other potential polymeric materials which may be used to form the drug matrix include ethylene-vinyl acetate copolymers, polypropylene, poly(vinyl)chloride, and cross-linked silicone prepolymers. Alternatively, various polymers may be blended to provide the desired monolithic matrix materials.

In another embodiment of the invention, the sterol\chemical modifier complex is contained with a liquid reservoir device. The liquid reservoir patch includes a backing material, a prodrug-containing reservoir, a rate-controlling membrane, a pressure-sensitive adhesive, and a release liner. In preparing liquid reservoir patches, the backing is heat sealed to the membrane to form a reservoir which can then be filled with a solution of the sterol complex, solvents, enhancers, gelling agent, stabilizer, and other excipients. In this embodiment, the prodrug solution contained within the reservoir should remain saturated, to provide a relatively constant release of prodrug through the intervening membrane.

The choice of membrane material will vary depending on the various patch components, the desired degree of permeability of the prodrug, compatibility with the prodrug solution, and mechanical considerations relating to patch construction. Permeable membrane materials suitable for use in the present invention include a wide variety of natural and synthetic polymers, such as polydimethylsiloxanes, ethylenevinylacetate copolymer (EVA), polyurethanes, polyurethane-polyether copolymers, polyethylenes, polyamides, polyvinylchlorides, polypropylenes, polycarbonates, and cellulosic materials, such as cellulose triacetate and cellulose nitrate/acetate, and hydrogels, such as 2-hydroxyethylmethacrylate (HEMA).

The patch may optionally contain additional components, such as preservatives or bacteriostatic agents, e.g., methyl hydroxybenzoate, chlorocresol, benzalkonium chlorides, and the like.

B. Active Transdermal Delivery

In a preferred embodiment, the sterol/chemical modifier complex is administered transdermally by iontophoresis. An typical iontophoretic device for administering the sterol prodrugs of the present invention is provided in FIG. 6.

Iontophoresis refers to the introduction, by means of an electric current, of ions of soluble salts into the tissues of the body. In iontophoretic delivery systems, an applied electric potential gradient is employed to enhance the transdermal delivery of ionized drug molecules. In the present invention, the ionized or ionizable drug molecule is preferably a charged sterol\chemical modifier complex. In a preferred embodiment, the charged molecule is a 17-O-derivatized prodrug of testosterone which exhibits enhanced iontophoretic transdermal flux over that of the unmodified parent compound.

An iontophoretic drug delivery system is generally composed of four basic components: a power source (typically batteries), control circuitry, electrodes, and two electrolyte-containing reservoirs.

Using FIG. 6 as an example, in a conventional arrangement, two electrodes are disposed so as to be in intimate contact with the skin of a subject, as illustrated by 11 and 13, the anode and cathode, respectively. Both electrodes are placed within a given skin region of the subject. One electrode is in contact with a reservoir containing the prodrug or donor reservoir 15, and the other is contained within a ground reservoir 17 containing a biocompatible electrolyte solution, such as sodium chloride. In the figure, the sterol-chemical modifier complex is designated as "D-C$^+$ A$^{31}$", with "D-C$^+$" representing the charged drug/chemical modifier portion of the complex. In the figure, "A$^{31}$" is the complex counterion.

The electrode in contact with the 17-sterol/chemical modifier complex is generally referred to as the "active" electrode 11. The active electrode is the one from which the prodrug is driven into the body by application of an electric gradient. In a preferred embodiment of the present invention, the prodrug is a positively charged quaternary ammonium derivative of testosterone and the active electrode is the anode. For iontophoretic delivery of sterol prodrugs which are negatively charged, the active electrode is the cathode.

The other electrode, contained within a second reservoir, is often referred to as the ground electrode 13, and serves to close the electrical circuit through the body. In some instances, delivery of the same drug out of both reservoirs in an alternating fashion can be carried out by periodically reversing the polarity of the electrodes.

A variety of electrode materials may be used in the iontophoretic delivery device, and range from materials such as platinum to silver-silver chloride. The choice of electrode will depend on the nature of the prodrug to be administered, among other considerations.

The active reservoir 15 will typically contain a solution of the prodrug species to be driven transdermally into the subject (including both the active species and accompanying counterions). The prodrug may be contained within an aqueous solution, or within a hydrophilic gel or gel matrix. In some instances, the active reservoir will contain the prodrug as a semi-solid, foam, or formulated with an absorbent material. The sterol prodrug may also be contained in a reservoir with a configuration such as those described for the passive transdermal patches above. The ground reservoir may similarly contain salt ions in an aqueous solution, or within a polymeric matrix.

Typically, the active reservoir will also contain buffers to maintain the reservoir environment at the same charge as the electrode. In most cases, a buffer possessing an opposite charge to the active prodrug will be employed. In some instances, depending on the counterion of the prodrug salt, the prodrug salt may act as its own buffer. In general, to achieve the highest transport efficiency, the concentration of all ionic species, with the exception of the sterol prodrug, is minimized.

In some embodiments of the invention, the iontophoretic device will optionally contain a selectively permeable membrane. The membrane may be located in a region separating the two reservoirs, or alternatively, may separate the contents of the active reservoir from the skin surface. Suitable materials for providing such membranes include many of the natural and synthetic polymers described above for inclusion in passive transdermal delivery systems.

In iontophoretically administering a sterol/chemical modifier complex to a subject, the circuit is completed by connection of the two electrodes to a source of electrical energy 19, such as a battery. An electronic control module is utilized to control the applied current, and in some cases, may comprise an integrated circuit, which would allow for varying time intervals or feedback-controlled drug delivery.

Transdermal iontophoretic delivery is accomplished by application of an electric current. In iontophoretic administration, drug or prodrug delivery rate is proportional to the amount of current applied.

In iontophoretically administering a 17-sterol prodrug of the present invention, an appropriate current intensity is selected which is below the pain threshold of the subject. The current should be within comfortable toleration of the patient, with a current density which is typically less than 0.5 mA/cm$^2$ of the electrode surface. The current is then applied for an appropriate length of time.

In a preferred embodiment of the invention, upon application of electric potential, positively charged prodrug ions at the active electrode (in this case, the anode) are driven from the donor reservoir, through the skin, and into the body. Simultaneously, negatively charged ions in the body of the subject will migrate from the body and into the donor reservoir. At the ground electrode (cathode in this case), negatively charged ions are driven into the skin, while positively charged ions from the body of the subject migrate into the ground reservoir. In order to maintain charge neutrality, oxidation occurs at the positive electrode and reduction at the negative electrode, as ions migrate from one side of skin to the other. Upon transport of the complex across the skin and into the bloodstream, cleavage occurs to release the parent sterol in active form.

The following examples illustrate, but in no way are intended to limit the scope of the present invention.

Materials and Methods

Testosterone was obtained from Sigma (St. Louis, Mo.).

$^1$H, $^{13}$C NMR spectra were obtained using a Gemini-400 spectrometer. Samples were typically dissolved in either deuterated DMSO or CDCl$_3$; TMS was used as an internal standard.

Thin layer chromatography (TLC) was typically performed using silica gel G-60 coated plates. TLC visualization was typically carried out using either anisaldehyde or Dragendorff's reagent, depending upon the nature of the analyte. Eluent systems were varied according to the polarity of the compounds analyzed.

TESTOSTERONE PRODRUGS POSSESSING CARBONATE LINKAGES TO TRIMETHYL AMMONIO-CONTAINING MODIFIERS

EXAMPLE 1

[2.0] Preparation of testosterone-17-β-N,N,N-trimethyl-L-serine methyl ester) carbonate, bromide salt The 17-hydroxyl group of testosterone was converted to the corresponding chloroformate ester by reaction with phosgene. A 1.93 molar solution (20 ml) of phosgene (35 mmol) dissolved in toluene was added dropwise to a solution of testosterone (1.101 g, 3.5 mmol) dissolved in 50 ml of tetrahydofuran. The resulting reaction mixture was stirred overnight. TLC analysis of the crude reaction mixture (eluent: 1:4 ethyl acetate/methylene chloride) indicated the disappearance of testosterone starting material. The volatile reaction components (solvent, excess phosgene) were removed in vacuo to yield the crude chloroformate ester derivative of testosterone.

The charged modifier portion of the conjugate was then introduced into the testosterone chloroformate intermediate by reaction with N,N-dimethylserine methyl ester. The crude chloroformate ester (1.4 g, 4.0 mmol) was dissolved in approximately 15 ml of methylene chloride, to which was added N,N-dimethylserine methyl ester (661 mg, 4.5 mmol), followed by addition of 4 ml of a methylene chloride solution containing 450 mg of triethylamine (TEA). The reaction mixture was stirred for 1 h at room temperature; TLC (SiO$_2$/1:4 ethyl acetate/methylene chloride) indicated the formation of a new product having an R$_f$ slightly lower than that of the testosterone intermediate starting material. The reaction mixture was then diluted with 60 ml of methylene chloride, and washed sequentially with brine, saturated sodium bicarbonate, and brine. The organic layer was then dried over anhydrous sodium sulfate and concentrated to yield essentially 100% of the crude N,N-dimethylserine methyl ester adduct, testosterone-17β-(N,N-dimethyl-L-serine methyl ester) carbonate. The product was purified by flash chromatography using a silanized column with methylene chloride as the eluent.

The N,N-dimethylserine methyl ester adduct was converted to the corresponding trimethylammonium derivative by reaction with an appropriate alkylating agent. To form the tetrafluoroborate salt of testosterone-17β-(N,N,N-trimethyl-L-serine methyl ester) carbonate, solid trimethyloxonium tetrafluoroborate (Aldrich, Milwaukee, Wis.) was added portionwise to a solution of the dimethylserine methyl ester adduct (231 mg, 0.5 mmol) in 6 ml of methylene chloride. The reaction mixture was vortexed and sonicated to aid in dissolution. The methylation reaction appeared to be essentially complete after 1 hour, based on TLC. The crude reaction mixture was evaporated to dryness and the crude quat salt triturated with diethyl ether to yield the resulting product, testosterone-17β-(N,N,N-trimethyl-L-serine methyl ester) carbonate, tetrafluoroborate salt(0.378 mmol, 75% yield). Chemical analysis and NMR verified the formation of the desired product.

Alternatively, the bromide salt of testosterone-17β-(N,N, N-trimethyl-L-serine methyl ester) carbonate was formed by treatment of an acetonitrile solution of the dimethyl-serine methyl ester adduct (230 mg, 0.5 mmol) with approximately 2 ml of a 2M solution of bromomethane in diethylether. The reaction mixture was stirred overnight and then concentrated to dryness. The remaining residue was triturated with ether, as above, to remove impurities and yield the desired product, testosterone-17β-(N,N,N-trimethyl-L-serine methyl ester) carbonate, bromide salt (0.16 mmol, 33% recovery).

EXAMPLE 2

[1.8] Preparation of testosterone-17β-{N-[6-(N,N,N trimethylammonio)hexanoyloxymethyl]glycinoyloxyethyl} carbonate, iodide salt To a solution of testosterone (1.154 g, 4 mmol) in 10 ml of methylene chloride maintained at 0° C., was added pyridine (480 mg, 6 mmol) and chloromethyl chloroformate (672, 5.2 mmol). After the addition was complete, the reaction mixture was allowed to warm to room temperature and stirred for an additional 2 h. The reaction mixture was then diluted by addition of 60 ml of methylene chloride, and washed sequentially with brine, 10% citric acid, brine, saturated sodium bicarbonate, and brine. The organic layer was then dried over sodium sulfate and concentrated in vacuo. The crude residue was recrystallized in hexane to yield the chloromethyl carbonate of testosterone (1.393 g, 3.7 mmol, 91% yield).

The chloromethyl carbonate intermediate was then converted to the corresponding iodo compound by addition of sodium iodide (2.4 g) to a solution of the chloromethyl carbonate in acetone (25 ml). The reaction mixture was refluxed for 2 hours, cooled, and evaporated to dryness. The residue was dissolved in methylene chloride (60 ml) and washed sequentially with brine and aqueous sodium thiosulfate. The organic layer was then dried over sodium sulfate and concentrated to yield the desired iodomethyl carbonate (1.66 g, 3.51 mmol, 96% yield).

To a solution of the iodomethyl carbonate (945 mg, 2 mmol) in acetonitrile was added O-(6-bromohexanoyloxymethyl)-N-carboxymethyl carbamate (630 mg, 2 mmol) and DIEA (N,N'-diisopropylethylamine, 388 mg, 3.0 mmol) dissolved in acetonitrile (5 ml). The reaction mixture was stirred at room temperature for 2 h and concentrated to dryness. The crude product was dissolved in 60 ml of methylene chloride and washed sequentially with brine, saturated sodium bicarbonate, 10% citric acid, and brine. The organic layer was dried over sodium sulfate and concentrated in vacuo. The crude residue was purified by flash column chromatography (eluent=3% methanol/methylene chloride) to yield the bromocarbamate carbonate testosterone intermediate, testosterone-17β-{N-[6-bromohexanoyloxymethyl]glycinoyloxymethyl}carbonate (776 mg, 60% yield).

The above bromo-containing intermediate was converted to the corresponding iodo compound by addition of sodium iodide (750 mg, 5 mmol) to a solution of the bromo carbamate intermediate (776 mg, 1.2 mmol) in acetone (15 ml). The reaction mixture was refluxed for 1.5 h to yield the corresponding iodo intermediate, testosterone-17β-{N-[6-iodohexanoyloxymethyl]glycinoyloxymethyl}carbonate, which was recovered in greater than 95% yield.

The iodocarbamate carbonate intermediate was then converted to the corresponding trimethylammonium compound by addition of trimethylamine (1.37 molar solution in acetonitrile) to a solution of the iodocarbamate carbonate intermednate (802 mg, 1.11 mmol) dissolved in acetonitrile (9 ml). The reaction mixture was stirred for 2 h at room temperature and concentrated to dryness. The crude quat salt product was purified by trituration with diethylether to yield the desired product, testosterone-17β-{N-[6-(N,N,N-trimethylammonio)-hexanoyloxymethyl]-glycinoyloxymethyl}carbonate, iodide salt (610 mg, 59% yield).

EXAMPLE 3

[1.4] Preparation of testosterone-17β-choline carbonate, bromide salt

2-Bromoethyl chloroformate (0.760 ml, 7.1 mmol) was added dropwise to a solution containing testosterone (1.00 g, 3.5 mmol) and pyridine (0.58 ml, 7.2 mmol) dissolved in anhydrous tetrahydrofuran (20 ml)/methylene chloride (10 ml). The reaction mixture was stirred for 2 h at room temperature and diluted by addition of methylene chloride. The organic layer was washed with 1N HCl, and the aqueous acidic layer extracted with methylene chloride. The organic extracts were combined, washed with saturated sodium bicarbonate, and dried over sodium sulfate. The organic layer was filtered and concentrated under vacuum to yield a crude oil. The oil was purified by column chromatography ($SiO_2$ column packing; eluent: 2.5% methanol in methylene chloride) to yield the desired bromoethyl carbonate intermediate (1.48 g, 96% yield).

A solution of trimethylamine (11.2 mmol) in acetonitrile (9 ml) was added via syringe to a solution of the bromoethyl carbonate intermediate (0.809 g, 1.84 mmol) in acetonitrile (8 ml). The reaction mixture was stirred at room temperature for approximately 15 h. A TLC taken at this time revealed the presence of unreacted starting material. Additional trimethylamine was added to the reaction mixture (5.6 mmol in 4.5 mL of acetonitrile) and the reaction mixture stirred for an additional 24 h. The reaction mixture was diluted with diethyl ether and the resulting precipitate separated by centrifugation. The precipitate was washed with ether and dried under vacuum to yield the desired quaternary ammonium bromide salt, testosterone-17β-choline carbonate, bromide salt (0.786 g, 86% yield).

EXAMPLE 4

[3.2] Preparation of testosterone-17β-[6-(N,N,N-trimethylammonio) hexanoyloxy-methyl]carbonate iodide salt Testosterone (1.0038 g, 3.481 mmol) was dissolved in methylene chloride (26 ml), cooled to 0° C., and stirred under an inert atmosphere. Pyridine (0.37 ml, 4.5 mmol) was added dropwise via syringe to the testosterone solution, followed by addition of a solution of chloromethyl chloroformate (0.593 g, 4.59 mmol) in methylene chloride (3.5 ml). The reaction mixture was allowed to warm to room temperature and stirred for an additional 2.25 h. The reaction mixture was diluted by addition of methylene chloride (15 ml) and the resulting solution washed with a solution of saturated sodium chloride, dried over sodium sulfate, and concentrated under vacuum to yield a solid residue. The crude solid was purified by column chromatography (silica gel support) to yield the chloromethyl carbonate ester of testosterone (1.113 g, 2.93 mmol, 84% yield).

The chloromethyl carbonate was converted to the corresponding iodomethyl carbonate by treatment with sodium iodide. The chloromethyl carbonate intermediate (1.106 g, 2.9 mmol) was dissolved in acetone (15 ml) and sodium iodide (1.701 g, 11.35 mmol) was added to the reaction flask. The resulting cloudy yellow solution was refluxed for approximately 2.5 h and concentrated under vacuum to form a red residue. The residue was dissolved in ethyl acetate (75 ml) and the resulting solution was then washed sequentially with water (75 ml), 5% sodium thiosulfate (2×75 ml), and saturated sodium chloride (75 ml) and dried over sodium sulfate. The organic layer was concentrated under vacuum to yield the desired crude solid product (1.37 g, essentially quantitative conversion).

The crude iodomethyl carbonate intermediate from above (1.37 g, 2.9 mmol) was dissolved in acetonitrile (66 ml), to which was added an acetonitrile solution containing 6-bromohexanoic acid (0.6277 g, 3.21 mmol) and DIEA (0.4143, 3.2 mmol). The reaction mixture was stirred at room temperature for 18.5 h and concentrated under vacuum. The residue was dissolved in ethyl acetate (75 ml) and the resulting organic layer was washed sequentially with a solution of saturated sodium chloride, saturated sodium bicarbonate, 5% sodium thiosulfate, 10% citric acid, and saturated sodium chloride. The organic layer was dried over sodium sulfate, decanted, and concentrated under vacuum. The crude oil was purified by column chromatography on silica gel (eluent: 5% methanol in methylene chloride) to yield the desired product, testosterone-17β-yl 6-bromohexanoyloxymethyl carbonate (1.455 g, 2.7 mmol, 93% yield).

The bromo carboxy carbonate derivative was then converted to the corresponding iodo compound by treatment with sodium iodide, as in Example 2 above. The desired iodo product, testosterone-17β-yl 6-iodohexanoyloxymethyl carbonate, was recovered in 94% yield.

The iodo carboxy carbonate adduct was then converted to the corresponding trimethylammonium compound by treatment with trimethylamine. A solution of trimethylamine (12.7 mmol) in acetonitrile (12 ml) was added to a solution of the iodo carboxy carbonate adduct (1.49 g, 2.5 mmol) in acetonitrile and the resulting mixture stirred for 15 h at room temperature. The mixture was concentrated under vacuum and the resulting residue then dissolved in a minimum volume of methylene chloride. The product-containing methylene chloride solution was then added dropwise, with stirring, into a flask containing ether, to precipitate the desired product. The sticky solid was triturated repeatedly with ether to yield a white solid, testosterone-17β-[6-(N,N,N-trimethylammonio)hexanoyloxymethyl]carbonate, iodide salt (1.47 g, 2.28 mmol, 90% yield).

EXAMPLE 5

[2.1] Preparation of testosterone-17β-(N,N,N-trimethyl-β-alaninyloxymethyl)carbonate, iodide salt Testosterone (1.001 g, 3.5 mmol) was transformed into the corresponding chloromethyl carbonate by treatment with chloromethyl chloroformate and pyridine, as described in Example 2 (product: 1.32 g, 3.47 mmol, 99% yield).

The chloromethyl carbonate intermediate was transformed into the corresponding iodomethyl carbonate (1.61 g, 100% yield) by treatment with sodium iodide, as described in Examples 2 and 4.

DIEA (0.565 ml, 3.24 mmol) was added to a solution of the above adduct, (1.40 g, 2.96 mmol) in acetonitrile (55 ml) and the resulting solution cooled to 0° C. in an ice bath. A solution of 3-chloropropionic acid (0.353 g, 3.26 mmol) in acetonitrile (20 ml) was added dropwise via syringe and the reaction mixture stirred for an additional 5.5 h at 0° C. The reaction mixture was concentrated under vacuum, dissolved in ethyl acetate and washed sequentially with saturated sodium bicarbonate, 10% citric acid, and saturated sodium chloride. The organic layer was dried over sodium sulfate, filtered, and concentrated under vacuum to yield the desired product, testosterone-17β-yl 3-chloropropanoyloxymethyl carbonate (0.435 g, 33% yield).

The above chloropropanoyloxymethyl carbonate derivative of testosterone was then converted to the corresponding iodo compound in essentially quantitative yield by treatment with sodium iodide in acetone, as described in Example 2.

The iodopropanoyloxymethyl carbonate derivative was converted to the corresponding quaternary ammonium salt by reaction with trimethylamine. A solution of trimethylamine (4.8 mmol) in acetonitrile (1.4M, 3.5 ml) was added dropwise to a solution of the iodopropanoyloxymethyl carbonate compound (0.5233 g, 0.96 mmol) in acetonitrile and the resulting reaction mixture stirred for an additional 3.25 h. The reaction mixture was concentrated under vacuum and the resulting residue was dissolved in a minimum amount of 5% methanol in methylene chloride and reprecipitated by addition to diethyl ether. The product was repeatedly triturated with ether to yield the desired product, testosterone-17β-(N,N,N-trimethyl-β-alaninyloxymethyl) carbonate, iodide salt (0.232 g, 40%).

EXAMPLE 6

[1.7] Preparation of testosterone-17β-(L-carnitine ethyl ester) carbonate, iodide salt Preparation of ethyl (4-N,N-dimethylamino-3-[R]-hydroxy)butanoate: To a solution of ethyl (4-chloro-3-[R]-hydroxy)butanoate (3 g, 18 mmol) in dimethylformamide (30 ml) was added sodium azide (6 g, 90 mmol), and the resulting mixture stirred for 6 h at 90° C. The solution was cooled to room temperature, poured into water, and extracted twice with diethyl ether. The combined ether extracts were dried over anhydrous magnesium sulfate and concentrated under vacuum to yield ethyl (4-azido-3-[R]-hydroxy)butanoate (3.6 g).

The azide was then transformed into the corresponding dimethylamino derivative. The crude azide (3.6 g) was dissolved in methanol (50 ml) and the resulting solution aspirated and filled with argon in a Parr hydrogenator bottle. To the above solution was added palladium on carbon, Pd/C (2.5 g, 10% palladium content), followed by addition of an aqueous formaldehyde solution (8 ml, 37% solution). The resulting mixture was then lightly pressurized with hydrogen gas, aspirated repeatedly, and finally pressurized to 50 psi and agitated for 3.5 h using a Parr hydrogenator. Upon completion, the resulting mixture was filtered through a celite pad and the filtrate concentrated under vacuum to form an oily residue (4.43 g). The product, ethyl (4-N,N-dimethylamino-3-[R]-hydroxy)butanoate, was purified by distillation (Kughelrohr, 2.12 g, 67% yield).

Preparation of the testosterone prodrug: To a solution of testosterone (2 g, 7.0 mmol) in tetrahydrofuran (50 ml) was added a 1.93M solution of phosgene in toluene (33 ml, 63 mmol). The solution was stirred for 4 h at room temperature, concentrated by rotary evaporation, and vacuum dried for approximately 30 minutes to yield the crude testosterone chloroformate adduct (2.88 g).

A solution of the testosterone chloroformate (1 g, 2.9 mmol) in methylene chloride (20 ml) was cooled to 0° C. To this solution was added dropwise a solution of ethyl (4-N,N-dimethylamino-3-[R]-hydroxy)butanoate (as prepared above, 1 g, 5.7 mmol) in methylene chloride (10 ml), and the resulting mixture was stirred for an additional 2 h at room temperature. The mixture was washed sequentially with water and saturated sodium bicarbonate, dried over sodium sulfate, and concentrated under vacuum (1.41 g). The crude residue was purified by column chromatography on silica gel (eluent: 5% methanol in methylene chloride) to yield the desired testosterone-17β-carbonate derivative (1.134 g).

Quaternization was carried out as follows. To a solution of the testosterone-17β-carbonate (1.13 g, 2.3 mmol) in acetonitrile (15 ml) was added methyl iodide (1.6 g, 11.3 mmol), and the resulting solution stirred for 2 h at room temperature. The reaction mixture was concentrated under reduced pressure. The resulting residue was dissolved in a minimum amount of methylene chloride and the resulting solution added dropwise to a stirred solution of diethyl ether. The precipitate was separated by centrifugation, and the recovered solid treated once more as described above. The product, testosterone-17β-(L-carnitine ethyl ester) carbonate, iodide salt, was dried under vacuum at 60° C. (1.3 g, 89% recovery). The precipitate was further purified by recrystallization from 60/40 isopropyl alcohol/ether.

EXAMPLE 7

[4.1] Preparation of testosterone-17β-(L-carnitine ethyl ester) carbonate, bromide salt The bromide salt of testosterone-17β-(L-carnitine ethyl ester) carbonate was similarly prepared. To a solution of the testosterone-17β-carbonate derivative (as prepared above, 574 mg, 1.174 mmol) in acetonitrile (5 ml) was added a 2 molar solution of bromomethane in ether (1 ml, 2 mmol). The resulting mixture was stirred for 4 h at room temperature and concentrated under vacuum. The remaining residue was dissolved in methylene chloride (5 ml) and added dropwise to a stirred solution of ether to precipitate the desired quat salt. The precipitate was collected by centrifugation, washed repeatedly with ether and dried in vacuo (0.595 g, 88% yield).

EXAMPLE 8

[3.4] Preparation of testosterone-17β-candicine carbonate, iodide salt

Testosterone chloroformate was prepared as follows. To a solution of testosterone (2 g, 7.0 mmol) dissolved in tetrahydrofuran (50 ml) was added a 1.93M solution of phosgene in toluene (33 ml). The resulting solution was stirred for 4 h at room temperature, concentrated under vacuum, and the resulting residue vacuum dried for approximately 30 minutes (2.88 g).

The above chloroformate was converted to the corresponding testosterone 17β-hordenine carbonate as follows. To a solution of hordenine (0.8 g, 4.8 mmol) and DIEA (0.6 g, 4.8 mmol) in methylene chloride (30 ml), cooled to 0° C., was added testosterone chloroformate (1.6 g, 4.6 mmol). The resulting reaction mixture was stirred for 1 h at room temperature and washed sequentially with water and sodium carbonate and dried over sodium sulfate. The crude solid (2.0 g) was purified by column chromatography (silica gel/15% methanol in methylene chloride) to yield the desired product, testosterone-17β-hordenine carbonate (1.8 g, 82% yield).

The testosterone hordenine carbonate adduct was methylated by addition of an excess of iodomethane (690 mg, 4.8 mmol) to a solution of the testosterone hordenine carbonate compound (0.870 g, 1.8 mmol) dissolved in acetonitrile (15 ml). The solution was stirred for 2 h at room temperature, during which time a white precipitate formed in the reaction flask. The solid was isolated, washed with ether and dried to yield the desired product, testosterone-17β-candicine carbonate, iodide salt (1.06 g, 95% yield).

TESTOSTERONE PRODRUGS POSSESSING CARBONATE LINKAGES TO AMINE SALT-CONTAINING MODIFIERS

EXAMPLE 9

[3.6] Preparation of testosterone-17β-(N,N-dimethyl-L-serine methyl ester) carbonate, hydrochloride salt As described in Example 1, the 17-hydroxy group of testosterone was converted to the corresponding chloroformate ester by reaction with phosgene, followed by treatment of the chloro ester intermediate with N,N-dimethylserine methyl ester to produce the desired N,N-dimethylserine methyl ester testosterone adduct in approximately 60% yield.

The N,N-dimethylserine methyl ester adduct (1.123 g) was dissolved in anhydrous tetrahydrofuran (45 ml) containing hydrogen chloride (2 mmol), which had been generated from the reaction of ammonium chloride and concentrated sulfuric acid. The resulting solution was stirred at room temperature for 10 minutes and concentrated under vacuum. The remaining residue was triturated with ether to yield the desired amine salt product (0.676 g, 1.36 mmol, 80% yield).

TESTOSTERONE PRODRUGS POSSESSING CARBONATE LINKAGES TO AMINO-CONTAINING MODIFIERS

EXAMPLE 10

[3.5] Preparation of testosterone-17β-N,N-dimethyl-L-serine methyl ester)carbonate The N,N-dimethylserine methyl ester carbonate adduct of testosterone was prepared as described in Example 1.

EXAMPLE 11

[3.3]Preparation of testosterone-17β-hordenine carbonate

The testosterone hordenine carbonate adduct was prepared as described in Example 8.

TESTOSTERONE PRODRUGS CONTAINING MULTIPLE CHARGED MODIFIERS

EXAMPLE 12

[4.4] Preparation of testosterone-3-enol, 17β-ol 3-(N,N,N-trimethyl-β-alanine ester) 17-(choline carbonate), dibromide salt Testosterone (1.0023 g, 3.47 mmol) was treated with 2-bromoethyl chloroformate and pyridine by the method described in Example 3 to form the corresponding bromoethyl carbonate intermediate. The carbonate intermediate was purified by column chromatography on silica gel using a mixed solvent eluent (30% ethyl acetate/70% hexane) to yield the desired product in essentially quantitative yield (1.527 g).

The reactant used for coupling the second modifier portion to testosterone, 3-bromopropanoic anhydride, was prepared as follows. A solution of DCC (dicyclohexylcarbodiimide, 1.180 g, 5.7 mmol) in anhydrous methylene chloride (5 ml) was added dropwise to a solution of 3-bromopropionic acid (1.754 g, 11.5 mmol) in methylene chloride (45 ml). The reaction mixture became cloudy immediately upon addition of the DCC and was allowed to stir at room temperature for an additional 3 h. The resulting mixture was filtered to yield a clear yellow solution which was concentrated under vacuum to form a yellow oil (1.6507 g, quantitative conversion). Formation of the anhydride was verified by $^1$H NMR; the anhydride product was used in subsequent transformations without further purification.

To a solution of the bromoethyl carbonate testosterone intermediate (1.527 g, 3.47 mmol) and p-toluenesulfonic acid monohydrate (0.099 g, 0.5205 mmol) in benzene (7 ml) was added a solution of 3-bromopropanoic anhydride (1.65 g, 5.73 mmol) in benzene (5 ml). The resulting mixture was gently refluxed for a total of 17 h. Upon cooling, the reaction mixture was diluted with benzene (10 ml) and washed sequentially with solutions of saturated sodium bicarbonate and saturated sodium chloride. The organic layer was dried over sodium sulfate, filtered, and concentrated under vacuum to yield an oil, which solidified upon storage in the refrigerator. The crude product was purified by column chromatography (silica gel; eluent: 20% ethyl acetate in hexane) to yield the desired 3-(3-bromo)propanoate ester, 17β-(2-bromo)ethyl carbonate bis adduct, (0.982 g, 49% yield).

The above bis adduct was then transformed to the corresponding bis quaternary ammonium compound. The above bis adduct (0.972 g, 1.692 mmol) was dissolved in acetonitrile, to which was added a 1.5M solution of trimethylamine in acetonitrile (16 ml, 24 mmol). The reaction mixture became cloudy upon addition of the amine, and was stirred for a total of 112 h. The mixture was diluted with diethylether (80 ml), and the resulting precipitate separated by centrifugation. The precipitate was triturated repeatedly with ether and dried under vacuum to yield the desired product, testosterone-3-enol, 17β-ol 3-(N,N,N-trimethyl-β-alanine ester) 17-(choline carbonate), dibromide salt, (0.941 g, 80% yield).

EXAMPLE 13

[4.3] Preparation of testosterone-3-enol, 17β-ol bis[4-(N,N,N-trimethylammonio)butyrate], dibromide salt Testosterone (1 g, 3.5 mmol), 4-bromobutanoic anhydride (1.2 g, 3.8 mmol), and benzene (10 ml) were added to a reaction flask and the resulting mixture refluxed for 3 h. The reaction mixture was cooled, washed with saturated sodium bicarbonate solution and dried over sodium sulfate. Concentration under vacuum resulted in 2.0 g of the desired product, testosterone-17β-(4-bromobutanoate).

Formation of the corresponding 3,17-bis adduct was carried out as follows. The following components were added to a reaction flask: testosterone-17-(4-bromobutanoate) (2 g, 3.5 mmol), 4-bromobutanoic anhydride (1.2 g, 3.8 mmol), benzene (10 ml), and p-toluenesulfonic acid (100 mg), and the resulting mixture was refluxed for 10 h. After cooling, the resulting solution was washed with saturated sodium bicarbonate solution, dried over sodium sulfate, decanted, and dried under vacuum. The resulting crude solid, testosterone-3,17β-bis(4-bromobutanoate), (3.0 g) was purified by column chromatography on silica gel (eluent: methylene chloride).

The testosterone-3,17β-bis(4-bromobutanoate) was converted to the corresponding bis quaternary ammonium compound by treatment with trimethylamine. To the bis(4-bromobutanoate) testosterone adduct (0.534 g, 0.91 mmol) was added a solution of trimethylamine in acetonitrile (1.37M, 5 ml) and the resulting mixture stirred for 1 h at 35° C. The resulting suspension was added to a stirred solution of ether (30 ml) and the white solid product collected by centrifugation and vacuum dried (0.550 g, 86% yield).

TESTOSTERONE PRODRUGS POSSESSING NEGATIVELY-CHARGED MODIFIERS

EXAMPLE 14

[4.2] Preparation of testosterone-17β-[taurine succinamide ester], triethylammonium salt To a solution of testosterone-17β-hemisuccinate, (250 mg, 643 mmol) (Sigma, St. Louis, Mo.) in dimethylformamide (3 ml) containing triethylamine (116 μL) was added EEDQ (N-ethyoxycarbonyl-2-ethoxy-1,2-dihydroquinoline, 230 mg, 0.93 mmol), followed by addition of taurine (80 mg, 0.643 mmol). The mixture was stirred for 1 h at 90° C., cooled, and added dropwise to a stirred solution of ether (40 ml). The milky solution was centrifuged and the resulting pellet dissolved in a minimum of methylene chloride. The methylene chloride solution was filtered to remove solid impurities and the filtrate was added dropwise to a stirred solution of ether (40 ml). The precipitate was collected following centrifugation and vacuum dried (124 mg, 32% yield).

TESTOSTERONE PRODRUGS POSSESSING CARBOXY LINKAGES TO TRIMETHYLAMMONIO-CONTAINING MODIFIERS

EXAMPLE 15

[2.5] Preparation of testosterone-17β-(N,N,N-trimethy-β-alaninyl ester), bromide salt To a cooled (0° C.) solution of testosterone (1 g, 3.5 mmol) in methylene chloride (5 ml) containing pyridine (0.247 g, 3.5 mmol) was added 3-bromopropanoyl chloride (0.600 g, 3.5 mmol) dissolved in methylene chloride (2 ml). The resulting solution was stirred for 1 h at room temperature, analyzed by TLC for extent of reaction, and additional acid chloride (3.5 mmol) and pyridine (3.5 mmol) added to the reaction flask. The mixture was stirred for an additional hour at room temperature, diluted with methylene chloride (30 ml) and washed sequentially with solutions of saturated sodium chloride, saturated sodium bicarbonate, and 1N HCl. The organic layer was dried over sodium sulfate, decanted, and concentrated under vacuum. The crude product (1.1 g), testosterone-17β-(3-bromopropanoate), was purified by treatment with activated charcoal, followed by trituration with hot methanol to give 0.620 g of product.

The bromoalkyl ester adduct of testosterone was then converted to the corresponding trimethylammonio compound. A 1.25M solution of trimethylamine in acetonitrile (3.5 ml, 4.41 mmol) was added to a solution of testosterone-17β-(3-bromopropanoate) (0.620 g, 1.47 mmol) dissolved in a mixed solvent system containing acetonitrile (5 ml) and tetrahydrofuran (2 ml). The reaction mixture was stirred for 12 h at room temperature and additional trimethylamine-acetonitrile (3.5 ml) added to the reaction flask. The reaction mixture was stirred for an additional 12 h. The resulting mixture was concentrated to dryness and the residue dissolved in 10% methanol in methylene chloride. The product-containing methylene chloride solution was added dropwise, with stirring, to a flask containing ether (50 ml). The resulting precipitate was collected and the process repeated. The product was dried in vacuo (0.508 g, 71% yield).

EXAMPLE 16

[2.2] Preparation of testosterone-17β-betainoyl ester, bromide salt

To a solution of testosterone (1.00 g, 3.5 mmol) in methylene chloride (20 ml) was added bromoacetyl chloride (0.550 g, 3.5 mmol). The solution was stirred for 12 h at room temperature, diluted by addition of methylene chloride (30 ml) and washed sequentially with solutions of saturated sodium bicarbonate and water, and the combined organic extracts dried over sodium sulfate. The solvent was removed by rotary evaporation. The product, testosterone-17β-(2-bromoethanoate), was recovered in 49% yield.

The above bromoalkyl ester adduct of testosterone was converted to the corresponding quaternary ammonium compound. To an ice cold solution of testosterone-17β-(2-bromoethanoate) (0.576 g, 1.406 mmol) in acetonitrile (5 ml) was added a 1.25M solution of trimethylamine in acetonitrile (3.4 ml). The reaction mixture was stirred for 2 h at room temperature, evaporated to dryness and the recovered residue dissolved in a minimum volume of methanol. The methanol solution was added dropwise to a flask containing ether (30 ml), and the milky suspension centrifuged to isolate the desired product. The process was repeated and the product dried in vacuo (650 mg).

EXAMPLE 17

[1.1] Preparation of testosterone-17β-(O-palmitoyl-L-carnitinate), chloride salt The acyl chloride of O-palmitoyl-[L]-carnitine was prepared by mixing O-palmitoyl-[L]-carnitine (1.5 g, 3.5 mmol) and oxalyl chloride (0.444 g, 3.5 mmol) in methylene chloride (10 ml). The resulting solution was added to a solution of testosterone (1.0 g, 3.5 mmol) in methylene chloride (15 ml) and the reaction mixture stirred for 12 h at room temperature. The mixture was filtered to remove hydrolyzed carnitine and the filtrate concentrated by rotary evaporation. The residue was dissolved in methylene chloride (10 ml) and added dropwise to a flask containing ether (60 ml) to precipitate the quaternary ammonium salt. The milky solution was centrifuged to isolate the product and the process repeated (1.02 g). The product was further purified by column chromatography on RP-2 silica gel using a gradient eluent system (400 ml methylene chloride, followed by 400 ml of 1% methanol in methylene chloride).

EXAMPLE 18

[3.8] Preparation of testosterone-17β-[(4-N,N,N-trimethylammonio) crotonate], chloride salt 4-N,N,N-trimethylammonio-2-butenoic acid, chloride salt (crotonyl betaine) was prepared according to the procedure of Brendel. A mixture containing L-carnitine (5 g, 25 mmol), acetic anhydride (50 ml), and acetic acid (50 ml) was refluxed for approximately 10 minutes, cooled, and the solvents removed by rotary evaporation under reduced pressure. The residue was recrystallized twice from isopropanol and dried in vacuo to yield the purified product (2.0 g).

The acid chloride of crotonylbetaine was prepared by mixing crotonylbetaine (0.621 g, 3.5 mmol) and oxalyl chloride (0.444 g, 3.5 mmol) in methylene chloride (5 ml), and the resulting acid chloride was added to a solution of testosterone (1.0 g, 3.5 mmol) in methylene chloride (15 ml). The reaction mixture was stirred to 6 h at 35°–40° C. to produce a nearly homogeneous yellow solution. The reaction was quenched by addition of one drop of water, and the mixture then evaporated to dryness. The residue was dissolved in methylene chloride, filtered to remove insoluble impurities, and the filtrate concentrated by rotary evaporation. The residue was dissolved in a minimum volume of methylene chloride and the product-containing solution added dropwise to ether (60 ml) to precipitate the quat salt, which was recovered by centrifugation. The product was washed with a 50/50 ether/hexane solvent mixture and dried in vacuo (1.18 g, 75%).

TESTOSTERONE PRODRUGS POSSESSING CARBOXY LINKAGES TO AMINE SALT-CONTAINING MODIFIERS

EXAMPLE 19

[3.1] Preparation of testosterone-17β-[4-N,N-dimethylaminobutyrate], hydrochloride salt One of the reactants, 4-(N,N-dimethylamino)butanoyl chloride, hydrogen chloride salt, was prepared as follows. 4-(N,N-dimethylamino)butanoic acid, HCl salt (0.684 g, 4.083 mmol) was suspended in methylene chloride (16 ml). Dimethylformamide (one drop) and oxalyl chloride (0.890 ml, 10.2 mmol) were added sequentially via syringe and the resulting mixture stirred at room temperature for 16.5 h. The mixture was concentrated by rotary evaporation, the residue was redissolved in methylene chloride, and concentrated under vacuum three times. The product was dried under high vacuum (0.7598 g, 95%) and used without further purification.

4-(N,N-dimethylamino)butanoyl chloride, hydrogen chloride salt, as prepared above (0.76 g, 4.084 mmol) was dissolved in methylene chloride (10 ml) and stirred under an inert atmosphere of argon. To this was added a solution of testosterone (0.9808 g, 3.4% mol) in methylene chloride (10 ml) and the reaction mixture stirred for a total of 5.75 h at room temperature. The mixture was concentrated under reduced pressure and the recovered residue further dried under high vacuum. The residue was rinsed with ether and recovered by centrifugation. The recovered solid was dissolved in methylene chloride containing 10% methanol, and the resulting solution added dropwise to stirred ether solution. The white precipitate was recovered by centrifugation and washed with ether; this process was repeated two more times and the recovered solid dried under high vacuum at 55° C. for several hours (1.4617 g, 98% yield).

EXAMPLE 20

[3.7] Preparation of testosterone-17β-nicotinate, hydrochloride salt

To a suspension of nicotinoyl chloride hydrochloride (720 mg, 4 mmol) in methylene chloride (10 ml) was added pyridine (320 mg, 4 mmol) and a solution of testosterone (1.00 g, 3.5 mmol) in methylene chloride. The resulting mixture was stirred at room temperature for 12 h, diluted by addition of methylene chloride, and the resulting solution washed with saturated sodium bicarbonate and brine. The aqueous layers were extracted with methylene chloride to ensure recovery of the product, and the combined organic extracts dried over sodium sulfate, decanted, and concentrated under vacuum. The crude solid, testosterone-17β-nicotinate, (1.17 g, 85% yield) was recrystallized from acetone.

The testosteryl ester was converted to the corresponding acid salt as follows. Testosterone-17β-nicotinate (870 mg) was dissolved in ethanol (120 ml) containing 400 µL of concentrated hydrochloric acid. The solution was evaporated to dryness and triturated with ether to yield the desired hydrogen chloride salt (96% yield).

EXAMPLE 21

[3.9] Preparation of testosterone-17β-picolinate, hydrochloride salt

Picolinoyl chloride was formed by slow, dropwise addition of dimethylformamide (6 drops) and oxalyl chloride (3.15 ml, 36 mmol) to a solution of picolinic acid (1.76 g, 14.3 mmol) in methylene chloride (60 ml). The reaction mixture was stirred at room temperature for 3 h. At this point, the mixture was carefully concentrated under vacuum and used without further purification.

To a suspension of picolinoyl chloride (2.1099 g, 11.8 mmol) in methylene chloride (30 ml) was added a solution of testosterone (2.85 g, 9.9 mmol) in methylene chloride. The resulting mixture was sonicated to aid in dissolution of the reactants. The reaction mixture was stirred for 17.5 h at room temperature, diluted with methylene chloride (75 ml), and washed sequentially with solutions of saturated sodium bicarbonate and brine. The organic extracts were combined, dried over sodium sulfate, filtered and concentrated under vacuum. The resulting black residue was purified by column chromatography on silica using a gradient eluent system (5% methanol in methylene chloride/10% methanol in methylene chloride). The recovered solid was dissolved in ethanol (100 ml) and acidified by addition of concentrated hydrochloric acid (10 ml). The resulting precipitate was recovered by centrifugation. The solid was purified by twice dissolving in a minimum amount of 10% methanol in methylene chloride and reprecipitating in ether. The product was dried under vacuum (3.36 g, 79% yield).

TESTOSTERONE PRODRUGS POSSESSING CARBOXY LINKAGES TO QUATERNARY AMMONIUM-CONTAINING HETEROARYL OR HETEROCYLIC MODIFIERS

EXAMPLE 22

[4.0] Preparation of testosterone-17β-(N-methylpicolinate), hydrogen sulfate salt Testosterone-17β-picolinoate was prepared as in Example 21. Dimethyl sulfate (0.100 ml, 1.057 mmol) was added to a solution of testosterone-17β-picolinate (0.2009 g, 0.5105 mmol) in anhydrous tetrahydrofuran. The reaction mixture was refluxed gently for 18 h, cooled, and concentrated under vacuum. The oily residue was dissolved in a minimum of methylene chloride and reprecipitated in ether several times and dried under high vacuum (0.0821 g, 32% yield).

EXAMPLE 23

[4.0] Preparation of testosterone-17β-(N-methylpicolinate), iodide salt

Testosterone-17β-picolinate was prepared as in Example 21 and converted to the corresponding N-methyl quaternary ammonium compound by treatment with iodomethane. To a solution of the testosterone picolinic ester (0.6734 g, 1.7 mmol) in acetonitrile (13 ml) was added iodomethane (1.06 ml, 17 mmol) and the resulting mixture heated to 40° C. The reaction mixture was stirred for approximately 23 h. additional iodomethane (1 ml) added to the reaction flask, and the reaction mixture stirred for an additional 23 h at 40° C. The mixture was concentrated by rotary evaporation. The residue was dissolved in methylene chloride containing a small quantity of methanol, and the solution added to a stirred solution of ether to precipitate the desired product. The product was triturated with ether, isolated by centrifugation, redissolved, and the process repeated twice more. The recovered iodide salt product was dried in a vacuum oven at 40° C. (0.8252 g, 90% yield).

EXAMPLE 24

[2.6] Preparation of testosterone-17β-[(O-acetyl)-betonicinyl ester], chloride salt 4-Acetoxy-N,N-dimethylproline trifluoroacetate was prepared as follows. 4-Hydroxy-N,N-dimethylproline (1.59 g, 0.01 mol) was added to trifluoroacetic acid (3 ml) and the resulting suspension stirred until dissolution was complete. Upon dissolution of the reactants, acetyl chloride (6 ml) was added to the reaction flask and the resulting mixture stirred for 12 h at 40°–46° C. The reaction mixture was cooled, concentrated by rotary evaporation, and the resulting residue diluted with acetone (20 ml). A milky suspension formed upon addition of the acetone solution to a stirred solution of ether. The solid was allowed to settle, the ether removed by decantation, and the white solid triturated twice with ether. The solid product was dried in vacuo at 80° C. (1.54 g).

The acid chloride of 4-acetoxy-N,N-dimethylproline was formed by addition of 4-acetoxy-N,N-dimethylproline trifluoroacetate (1.1 g, 3.5 mmol) to oxalyl chloride (0.444 g, 3.5 mmol) in methylene chloride (5 ml), and the resulting solution added dropwise to a solution of testosterone (1.0 g, 3.5 mmol) in methylene chloride (5 ml). The reaction mixture was stirred for 12 h at room temperature and the resulting green solution concentrated under vacuum. The residue was dissolved in methylene chloride (5 ml), added dropwise to ether (60 ml), and the resulting precipitate collected by centrifugation. The process was repeated and the solid product dried in vacuo at 60° C. (1.5 g). The product was purified by column chromatography (SiO$_2$-RP-2/methylene chloride)( 660 mg, 40% yield).

EXAMPLE 25

[2.9] Preparation of testosterone-17β-stachydrine ester, chloride salt

Stachydrine was converted to the corresponding acid chloride. To a suspension of stachydrine (1.246 g, 8.7 mmol) in methylene chloride was added dimethylformamide (2 drops), followed by dropwise addition of oxalyl chloride (1.90 ml, 21.78 mmol). The addition of oxalyl chloride resulted in vigorous bubbling. After approximately 10 minutes, the reactants were all dissolved. The reaction was stirred for an additional 3 h at room temperature and concentrated under reduced pressure to yield a thick oil. The oil was dissolved in dry methylene chloride and the resulting solution concentrated. This process was repeated two more times and resulted in a solid product, which was further dried under high vacuum. The desired acid chloride product (1.723 g) was used without further purification.

The acid chloride was dissolved in methylene chloride (16 ml), to which was added a solution of testosterone (2.1304 g, 7.38 mmol) in methylene chloride (10 ml). The reaction flask was flushed with argon and the reaction mixture stirred for 16 h. The mixture was concentrated and the residue dried under high vacuum. The product was dissolved in methylene chloride-methanol and reprecipitated from ether. The sticky precipitate was agitated in ether to form a white powdery solid. This process of dissolution-precipitation was repeated two times and the recovered solid dried under high vacuum (2.666 g, 80% yield).

IN VITRO ASSAYS

EXAMPLE 26

Determination of Testosterone Prodrug Hydrolysis in Serum

Stock solutions (6 mM) of the testosterone prodrugs were prepared in ethanol (dissolution was accomplished by vortexing, sonication, or warming at 37° C., as needed). If required for dissolution, one drop of a co-solvent such as dimethylsulfoxide, dimethylformamide or methanol was added. (Acetonitrile is undesirable because it deactivates the serum enzymes).

HPLC separation methods were established for each study by dilution of the above stock solutions (6 μl) in acetonitrile (1 ml) to form 36 μM solutions. Samples (10 μl) were injected onto a Nucleosil 5C8 column (250×4 mm ID) fitted with an additional guard column (11×4 mm ID) and eluted with a mobile phase of approximately 65% HPLC grade water and 35% trifluoroacetic acid in acetonitrile (0.1% TFA in acetonitrile). Exact proportions of the mobile phase eluents were adjusted in each case to give optimum separation and run times.

Freshly defrosted human serum (3 ml, Sigma) was warmed at 37° C. for five minutes and then the testosterone prodrug stock solution (60 μl) was added with vortexing. Incubation at 37° C. was continued and aliquots (400 μl) were removed at six appropriate time points based on $t_{1/2}$'s estimated from a preliminary one point study. The aliquots were added to 800 μl of 2% zinc sulfate solution in a 1.5 ml disposable microcentrifuge tube, vortexed immediately and centrifuged at 14,000 RPM for 3 minutes. The supernatants (10 μl) were injected onto the HPLC and peak areas used to determine the percent of parent drug formed or percent of prodrug remaining. Serum blanks were prepared similarly by addition of serum to the zinc sulfate solution, followed by centrifugation. Initial (time=0) samples were prepared by adding serum to the zinc sulfate solution, followed by addition of the complex and separation by centrifugation. The time=0 samples, as well as the original stock solutions, were also used to assess the stability of the complex in the absence of enzyme. Half-lives were determined using the following equation:

$$y - \ln 50 = 3.912 = mx + b,$$

and plotting time (x ordinate) versus the natural logarithm of percent remaining prodrug (y ordinate) to obtain the slope (m) and the y intercept (b). The serum half-lives of prodrug derivatives of testosterone are given in Table I.

TABLE 1

SERUM HALF-LIVES FOR TESTOSTERONE PRODRUGS
(TESTOSTERONE -17-B-O-R)

| Code | —R | —X | Serum Halflife | % Purity |
|---|---|---|---|---|
| 1.0 | —H | — | — | 99 |
| 1.1 | —COCH$_2$CH[OCO(CH$_2$)$_{14}$Me]CH$_2$N$^+$Me$_3$ | Cl— | 4.9 days | 91 |
| 1.2 | —COCH$_2$CH[OCOMe]CH$_2$N$^+$Me$_3$ | Cl— | 4 days | 96 |
| 1.3 | —COOCH$_2$OCO(CH$_2$)$_5$N$^+$Me$_3$ | Br/I— | 19 min. | 95 |
| 1.4 | —COO(CH$_2$)$_2$N$^+$Me$_3$ | Br— | 29 min. | 100 |
|  |  |  | 24 min. | 100 |
| 1.5 | —COOCH$_2$OCOCH$_2$N$^+$Me$_3$ | I— | 38 sec. | 84 |
| 1.6 | —COOCH$_2$OCOCH$_2$OCOCH$_2$N$^+$Me$_3$ | I— | 8.5 min. | 57 |
| 1.7 | —COOCH(CH$_2$COOCH$_2$Me)CH$_2$N$^+$Me$_3$ | I— | 49 min. | 77 |
|  |  |  | 4.2 hrs. | 82 |
| 1.8 | —COOCH$_2$OCOCH$_2$NHCOOCH$_2$—OCO(CH$_2$)$_5$N$^+$Me$_3$ | I— | 4.0 min. | 91 |
| 1.9 | —COOCH$_2$CH(COOMe)N$^+$Me$_3$ | BF$_4^-$ | ~4.5 sec. | 92 |
| 2.0 | —COOCH$_2$CH(COOMe)N$^+$Me$_3$ | Br$^-$ | 5 sec. | 39 |
| 2.1 | —COOCH$_2$OCO(CH$_2$)$_2$N$^+$Me$_3$ | I— | 38 sec. | 97 |
| 2.2 | —COCH$_2$N$^+$Me$_3$ | Br— | 14 hr. | 100 |
| 2.3 | —CO(CH$_2$)$_3$N$^+$Me$_3$ | Br— | ~15 hr.[1] | 99 |
| 2.4 | —CO(CH$_2$)$_4$N$^+$Me$_3$ | Br— | ~30 days | 100 |
| 2.5 | —CO(CH$_2$)$_2$N$^+$Me$_3$ | Br— | ~10 min[1]. | 97 |
| 2.6 | -[O-acetylbetonicine] | Cl— | 8.2 hr. | 97 |
| 2.7 | -nicotinate | — | ~5 wk. | 100 |

TABLE 1-continued

SERUM HALF-LIVES FOR TESTOSTERONE PRODRUGS
(TESTOSTERONE -17-B-O-R)

| Code | —R | —X | Serum Halflife | % Purity |
|---|---|---|---|---|
| 2.8 | -trigonelline | I— | 25.5 hr. | 100 |
| 2.9 | —L-stachydrine | Cl— | 13.7 hr. | 100 |
| 3.0 | —CO(CH$_2$)$_3$NMe$_2$ | — | 4.4 days$^2$ | 99 |
| 3.1 | —CO(CH$_2$)$_3$N$^+$HMe$_2$ | Cl— | 4.0 days$^2$ | 99 |
| 3.2 | —COOCH$_2$OCO(CH$_2$)$_5$N$^+$Me$_3$ | I— | 13 min. | 99 |
| 3.3 | -hordenine | — | 8.2 hr. | 99 |
| 3.4 | -candicine | I— | 5.8 hr. | 96 |
| 3.5 | —COOCH$_2$CH(COOMe)NMe$_2$ | — | 47 min. | 95 |
| 3.6 | —COOCH$_2$CH(COOMe)N$^+$HMe$_2$ | Cl— | 45 min. | 99 |
| 3.7 | -nicotinate, HCl | Cl— | ~5 wk. | 99 |
| 3.8 | —COCH=CHCH$_2$N$^+$Me$_3$ (salt) | Cl— | 5.1 days | 96 |
| 3.9 | -picolinate, HCl | Cl— | 12.2 hr. | 98 |
| 4.0 | —N-methylpicolinate | I— | 70 min. | 100 |
|  |  | HSO$_4^-$ | 65 min. | 97 |
| 4.1 | —COOCH(CH$_2$COOC$_2$H$_5$)CH$_2$N$^+$ME$_3$ | Br— | 4.0 hr. | 83 |
| 4.2 | —CO(CH$_2$)$_2$CONH(CH$_2$)$_2$SO$_3^-$ | N$^+$HE$^3$ | 24 hr. | 100 |
| 4.3 | 3,17β-bis-(CO(CH$_2$)$_3$N$^+$Me$_3$) | 2Br— | 7.8 hr.$^3$ | 94 |
| 4.4 | 17β-COO(CH$_2$)$_2$N$^+$Me$_3$<br>3-[CO(CH$_2$)$_2$N$^+$Me$_3$] | 2Br— | 2.3 min.$^1$ | 94 |

$^1$prodrug remaining, no testosterone formed.
$^2$prodrug remaining, ~50% testosterone and ~50% unknown formed.
$^3$prodrug remaining, 60% [2.3] formed, no other products seen.

EXAMPLE 27

Cytotoxicity Evaluation of Testosterone Prodrugs

The viability of human dermal fibroblasts in the presence of the 17-hydroxy sterol/chemical modifier compounds was assayed using MTT (3-[4,5-dimethylthiazol-2-yl]-2,5-diphenyltetrazolium bromide) reduction to formazan by mitochondrial enzymes as an indicator of cytotoxicity (Swisher, et al.). Confluent fibroblast cells were incubated for 2 or 16 hours in the presence of increasing concentrations of drug complex. At the end of the incubation period, medium was replaced for 4 hours by medium containing the tetrazolium salt, MTT. Metabolism of MTT to a blue formazan was quantitated by spectrophotometry at 540 nm. Inhibitory concentration 50% (IC50) values represent the molar concentration of the drug compound required to kill 50% of fibroblast cells.

TABLE 2

IN VITRO KERATINOCYTE CYTOXICITY

| Compound Code | IC$_{50}$ 2 h | IC$_{50}$ 16 h | H$_2$O sol (mg/ml) | Degradation (%/d) |
|---|---|---|---|---|
| 1.4 | 9.66E-04 | 9.29E-04 | 4.0 | 0 |
| 1.7 | 9.13E-04 | 8.49E-04 | 5.3 | 0 |
| 2.9 | 2.13E-03 | 7.50E-04 | 22.0 | 0 |
| 2.2 | 2.30E-03 | 6.50E-04 | 10.0 | 0 |
| 3.8 | 2.29E-03 | 5.83E-04 | 21.0 | 0 |
| 2.4 | 6.09E-04 | 5.68E-04 | 18.0 | 0 |
| 4.1 | 1.40E-03 | 5.60E-04 | 21.0 | 1 |
| 2.8 | 5.98E-04 | 4.92E-04 | 0.8 | 0 |
| 1.0 | >1E-3 | 4.23E-04 | 0.0 | 0 |
| 3.2 | 6.15E-04 | 4.06E-04 | 20.0 | 77 |
| 2.5 | >6E-4 | 3.29E-04 | 0.3 | 0 |
| 2.6 | 7.33E-04 | 2.71E-04 | 21.0 | 0 |
| 2.3 | 6.53E-04 | 1.72E-04 | 20.0 | 0 |
| 3.6 | 2.24E-04 | 1.57E-04 | 20.0 | 3.8 |
| 3.1 | 2.55E-04 | 1.45E-04 | 22.0 | 0 |
| 3.4 | 5.44E-04 | 4.46E-05 | 0.1 | 1 |
| 4.0* | 3.30E-04 | 4.11E-05 | 0.9 | 6 |
| 1.2 | 9.16E-05 | 3.44E-05 | 22.0 | 0 |
| 2.7 | >1E-3 | >1E-3 | 0.0 | — |
| 1.1 | <1E-5 | <1E-5 | 26.0 | 0 |

*iodide salt.

EXAMPLE 28

Electrotransport Flux Across Hairless Mouse Skin

A. Electrotransport Cell Construction

The electrotransport of testosterone/chemical modifier complexes was achieved using modified Valia-Chien cells (1.0 ml donor and 2.5 ml receptor cells). Full thickness, hairless mouse skin (Charles River Labs, Wilmington, Mass.) was soaked for one hour in phosphate buffered saline (PBS, pH=7.4) before placing between each compartment (dermal side of skin facing toward receptor). One passive (P1:data) and two or more (ET$_m$:data) active cells were used to screen each compound.

B. Donor/Receptor Preparation

A 10 mM (1 ml) aqueous solution of testosterone drug/prodrug was placed in the donor (unstirred) compartment and the receptor (stirred) was filled with 2.5 ml of PBS. In order to check for egress due to e.g. damaged skin, a zero hour sample of receptor (200 ml) was taken one half hour after the drug solution was placed in the donor compartment. Replacement fluid of equal sample volume was added to the receptor compartment immediately after samples were taken.

C. Electrochemistry

Anodic electrotransport was achieved using a silver wire (immersed in a polyvinylalcohol-based salt bridge to minimize junction potential) in the donor compartment and a AgCl cathode in the receptor. Cathodic transport was achieved with the electrode configuration reversed (silver wire in receptor, AgCl in donor). The electrotransport cells were connected in series and constant current (100 uA/cm$^2$, 58 uA for a skin area of 0.64 cm$^2$) and temperature (32° C.) were supplied to each cell. After six hours of active/passive transport, aliquots (200 ul) of the receptor were sampled and immediately analyzed by HPLC.

D. Analysis of Samples

A standard plot of peak area and concentration for each compound was constructed using HPLC. The peak areas of the samples were determined and the concentrations calculated using the standard data. Cumulative flux was calculated using Quickbasic and reported in nmol/cm$^2$/hr.

TABLE 4

STEADY STATE FLUX (HUMAN SKIN) FOR TESTOSTERONE PRODRUGS, TESTOSTERONE-17B-O-R

| Compound ID # | R | Steady State Flux (nmole/cm$^2$/h) |
|---|---|---|
| 1.4 | —COO(CH$_2$)$_2$N$^+$Me$_3$ | 68 ± 4 |
| 1.7 | —COOCH(CH$_2$COOCH$_2$Me)CH$_2$N$^+$Me$_3$ | 75 ± 14 |
| 2.9 | -L-stachydrine | 184 ± 30 |

TABLE 3

ELECTROTRANSPORT SKIN FLUX FOR TESTOSTERONE PRODRUGS (Murine Skin)

| Code | —R | —X | Flux (nmol/cm$^2$/hr) |
|---|---|---|---|
| 1.0 | —H | — | ET3: 1.0 ± 0.1, P1: 1.0 |
| 1.1 | —COCH$_2$CH[OCO(CH$_2$)$_{14}$Me]CH$_2$N$^+$Me$_3$ | Cl— | ET4: 0 |
| 1.2 | —COCH$_2$CH[OCOMe]CH$_2$N$^+$Me$_3$ | Cl— | ET4: 7.3 ± 5.8 |
| 1.4 | —COO(CH$_2$)$_2$N$^+$Me$_3$ | Br— | ET13: 20.8 ± 21.0, P7: 4.0 ± 0.8 |
| 1.7 | —COOCH(CH$_2$COOCH$_2$Me)CH$_2$N$^+$Me$_3$ | I— | ET3: 3.6 ± 1.3, P1: 1.1 |
| 1.8 | —COOCH$_2$OCOCH$_2$NHCOOCH$_2$—OCO(CH$_2$)$_5$N$^+$Me$_3$ | I— | ET3: 0.8 ± 0.1T, P1: 0.5T |
| 2.1 | —COOCH$_2$OCO(CH$_2$)$_2$N$^+$Me$_3$ | I— | ET3: 5.3 ± 0.6T, P1: 0.6T |
| 2.2 | —COCH$_2$N$^+$Me$_3$ | Br— | ET4: 7.9 ± 4.1, P4: 0 |
| 2.3 | —CO(CH$_2$)$_3$N$^+$Me$_3$ | Br— | ET3: 2.0 ± 0.8, P1: 0.5 |
| 2.4 | —CO(CH$_2$)$_4$N$^+$Me$_3$ | Br— | ET3: 2.7 ± 1.1, P1: 0 |
| 2.5 | —CO(CH$_2$)$_2$N$^+$Me$_3$ | Br— | ET2: 18.0 ± 2.4, P1: 1.0 |
| 2.6 | -[O-acetylbetonicine] | Cl— | ET3: 0, P1: 0 |
| 2.8 | -trigonelline | I— | ET3: 3.1 ± 1.2, P1: 0.2 |
| 2.9 | —L-stachydrine | Cl— | ET3: 3.25.3, P1: 0.6 |
| 3.1 | —CO(CH$_2$)$_3$N$^+$HMe$_2$ | Cl— | ET3: 0.7 ± 0.2, P1 0.3 |
| 3.2 | —COOCH$_2$OCO(CH$_2$)$_5$N$^+$Me$_3$ | I— | ET3: 4.8 ± 0.6, P1: 0.3 |
| 3.3 | -hordenine | — | ET3: 1.3 ± 0.6T, P1: 0 |
| 3.4 | -candicine | I— | ET3: 0, P1: 0 |
| 3.6 | —COOCH$_2$CH(COOMe)N$^+$HMe$_2$ | Cl— | ET3: 6.8 ± 0.3, P1: 4.7 |
| 3.8 | —COCH=CHCH$_2$N$^+$Me$_3$ (salt) | Cl— | ET3: 9.4 ± 1.2, P1: 0.7 |
| 4.0 | —N-methylpicolinate | I— | ET3: 0.71 ± 0.3, P1: 0.2 |
| 4.1 | —COOCH(CH$_2$COOC$_2$H$_5$)CH$_2$N$^+$Me$_3$ | Br— | ET3: 15.7 ± 5.3, P1: 0.2 |
| 4.2 | —CO(CH$_2$)$_2$CONH(CH$_2$)$_2$SO$_3^-$ | HNEt$_3^+$ | ET3: 2.8 ± 3.7, P1: 0 |
| 4.3 | 3,17β-bis-(—CO(CH$_2$)$_3$N$^+$Me$_3$) | 2Br— | ET3: 1.0 ± 0.6, P1: 4.0 |
| 4.4 | 17β-COO(CH$_2$)$_2$N$^+$Me$_3$ 3-[CO(CH$_2$)$_2$N$^+$Me$_3$] | 2Br— | ET3: 0.2 ± 0.0, P1: 1.0 |

EXAMPLE 29

Steady State Flux Across Human Skin

Iontophoretically-induced steady state flux across human skin was determined for three distinct testosterone/chemical modifier complexes, testosterone-17β-stachydrine ester, chloride salt [2.9], testosterone-17β-(L-carnitine ethyl ester) carbonate, iodide salt [1.7], and testosterone-17β-choline carbonate, bromide salt [1.4]. The in vitro skin flux experiments were carried out in a similar fashion to those described above, with the exception that human skin was used as the membrane.

Steady state flux values provide an indication of the total amount of drug (or drug complex) that can penetrate the skin, under a given set of experimental conditions. Steady state flux values for three testosterone/chemical modifier complexes under evaluation are shown in Table 4 below.

The flux values illustrate the feasibility of iontophoretically delivering the modified testosterone complexes of the present invention.

IN VIVO ASSAY

EXAMPLE 30

Determination of Plasma Concentrations of Testosterone Prodrugs and Their Metabolites Following Iontophoretic Transdermal Delivery In vivo iontophoretic delivery of the testosterone prodrugs is typically carried out with a battery-powered control module and two hydrogel-electrode patches. The power source is a one-channel constant-current device compliant to within 5 percent of the set point value and can contain a current of up to 2 mA into a resistive load of 10 kiloohms.

The hydrogel-electrode patches consist of a conductive polyvinyl acetate (PVA) hydrogel matrix that is in contact with a metallic electrode mesh and is housed in a circular section of polyethylene foam tape. The hydrogel contact area with the skin is 25 cm² although patch aea may be varied as needed. The "active" patch has a silver electrode and a hydrogel matrix composed of 26% testosterone prodrug, 15% PVA and 59% water by weight. The other patch has a silver chloride electrode and a hydrogel matrix composed of 2% sodium chloride, 15% PVA and 83% water by weight. The hydrogel formulations are prepared by dissolving PVA in water at 90° C. adding the appropriate substrate, pouring the solution in electrode housings, and freezing at −20° C. for a minimum of 4 h.

Using electric clippers, hair is removed from the dorsal surface of weaning pigs weighing between 6 and 12 kg. The clipped regions are cleaned with wet gauze and dried. The hydrogel patches are then pressed into place. The appropriate lead wires from the control module are connected to the two patches and the control module is taped securely to the back of the pig.

Iontophoretic delivery of the testosterone prodrug is performed at currents of up to 1 mA for a duration of 24 h. After initiating iontophoresis, blood samples are withdrawn every 2 h by means of an indwelling jugular catheter. Each pig is utilized on consecutive days for two iontophoretic studies at two different currents. New skin sites and new patches are used for each experiment.

Blood samples are hepararinized and centrifuged, and the plasma is stored at −80° C. Plasma concentrations of testosterone, the chemical modifier portion(s), optional spacer groups, and the testosterone prodrug are determined by HPLC. The area under the plasma concentration versus time curve is used to estimate the value of the systemic clearance for each pig.

It is claimed:

1. A composition for use in iontophoretic delivery to a subject, comprising:

a 17-hydroxy sterol/chemical modifier complex of the formula:

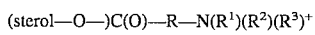

where C(O)—R—N(R$^1$)(R$^2$)(R$^3$)$^+$ represents the portion of the complex derived from the chemical modifier, —N(R$^1$)(R$^2$)(R$^3$)$^+$ is a quarternary ammonium group and R$^1$, R$^2$, and R$^3$ are independently selected from the group consisting of lower alkyl, alkyl, aryl, arylalkyl, cycloalkyl, heteroalkyl, and heteroarylalkyl; or R$^1$ and R$^2$ together with the nitrogen to which the are attached form a substituted heterocycle and R$^3$ is lower alkyl;

R is a linking moiety, linking the (sterol—O—)—C(O)— to the nitrogen atom;

where said complex is characterized by (i) a physiologically cleavable bond between the sterol and the chemical modifier, and (ii) enhanced iontophoretic transdermal uptake of the complex as compared to the 17-hydroxy sterol;

wherein lower alkyl is selected from the group consisting of methyl, ethyl, n-propyl and isopropyl;

wherein alkyl is selected from the group consisting of straight or branched alkyl chains having from 4 to 20 carbons;

wherein cylcloalkyl is selected from the group consisting of cyclic alkyl ring structures having between 3 to 10 carbons;

wherein R is selected from the group consisting of straight or branched acylalkyl chains and straight or branched acylalkyl chains with additional functional group or groups present internally; wherein said functionality is selected from the group consisting of carboxy, carbonate, carbamate, and amide;

wherein R contains an oxygen atom or a nitrogen atom connected to the carbonyl carbon to provide a carbonate or carbamate linkage, respectively;

wherein the chemical modifier/17-hydroxy sterol complex enhances the iotophoretic transport compared to said 17-hydroxy sterol alone.

wherein said chemical modifier has a charge to mass ratio of at least one charge to 1000.

2. The composition of claim 1, where R$^1$, R$^2$ and R$^3$ are independently lower alkyl.

3. The composition of claim 1, where R$^1$, R$^2$ and R$^3$ are independently selected from the group consisting of methyl, ethyl, n-propyl and isopropyl.

4. The composition of claim 1, where R contains an oxygen atom or a nitrogen atom connected to the carbonyl carbon to provide a carbonate or carbamate linkage, respectively.

5. The composition of claim 1, where R contains at least one internal functionality selected from the group consisting of carboxy, carbonate, carbamate, and amide.

6. The composition of claim 1, where R$^1$ and R$^2$ together with the nitrogen to which they are attached form a substituted aromatic heterocycle.

7. The composition of claim 1, where the chemical modifier is selected from the group consisting of stachydrine, O-acetylbetonicine, nicotinic acid, trigonelline, picolinic acid and N-methylpicolinic acid.

8. The composition of claim 1 where —R—N(R$^1$)(R$^2$)(R$^3$)$^+$ is N-methylhordenine.

9. The composition of claim 1 in which the 17-hydroxy sterol possesses a second derivatizable group having a second chemical modifier attached thereto;

wherein said second chemical modifier is covalently linked through said second derivatizable functional group of said 17-hydroxy sterol; and wherein said second chemical modifier's covalent link to the 17-hydroxy sterol is physiolgically cleavable.

10. The composition of claim 1, wherein the 17-hydroxy sterol is testosterone.

11. The composition of claim 1, wherein the chemical modifier is an N-alkylated amino acid salt.

12. A method for enhancing the transdermal electrotransport of 17-hydroxy sterol comprising:

modifying the sterol to produce a 17-hydroxy/sterol-chemical modifier complex of the formula:

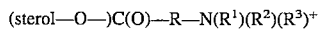

where C(O)—R—N(R$^1$)(R$^2$)(R$^3$)$^+$ represents the portion of the complex derived from the chemical modifier, —N(R$^1$)(R$^2$)(R$^3$)$^+$ is a quarternary ammonium group and R$^1$, R$^2$, and R$^3$ are independently selected from the group consisting of lower alkyl, alkyl, aryl, arylalkyl, cycloalkyl, heteroalkyl, and heteroarylalkyl; or R$^1$ and R$^2$ together with the nitrogen to which the are attached form a substituted heterocycle and R$^3$ is lower alkyl;

R is a linking moiety, linking the (sterol—O—)—C(O)— to the nitrogen atom;

where said complex is characterized by (i) a physiologically cleavable bond between the sterol and the chemical modifier, and (ii) enhanced iontophoretic transdermal uptake of the complex as compared to the 17hydroxy sterol;

wherein lower alkyl is selected from the group consisting of methyl, ethyl, n-propyl and isopropyl;

wherein alkyl is selected from the group consisting of straight or branched alkyl chains having from 4 to 20 carbons;

wherein cylcloalkyl is selected from the group consisting of cyclic alkyl ring structures having between 3 to 10 carbons;

wherein R is selected from the group consisting of straight or branched acylalkyl chains and straight or branched acylalkyl chains with additional functional group or groups present internally; wherein said functionality is selected from the group consisting of carboxy, carbonate, carbamate, and amide;

wherein R contains an oxygen atom or a nitrogen atom connected to the carbonyl carbon to provide a carbonate or carbamate linkage, respectively;

wherein the chemical modifier/17-hydroxy sterol complex enhances the iotophoretic transport compared to Said 17-hydroxy sterol alone.

wherein said chemical modifier has a charge to mass ratio of at least one charge to 1000.

13. A method of transdermally administering a 17-hydroxy sterol to a subject comprising:

iontophoretically administering to the subject a 17-hydroxy sterol/chemical modifier complex having the formula:

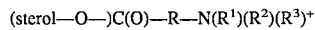
(sterol—O—)C(O)—R—N($R^1$)($R^2$)($R^3$)$^+$ where C(O)—R—N($R^1$)($R^2$)($R^3$)$^+$ represents the portion of the complex derived from the chemical modifier, —N($R^1$)($R^2$)($R^3$)$^+$ is a quarternary ammonium group and $R^2$, $R^2$, and $R^3$ are independently selected from the group consisting of lower alkyl, alkyl, aryl, arylalkyl, cycloalkyl, heteroalkyl, and heteroarylalkyl; or $R^1$ and $R^2$ together with the nitrogen to which the are attached form a substituted heterocycle and $R^3$ is lower alkyl;

R is a linking moiety, linking the (sterol—O—)—C(O)— to the nitrogen atom;

where said complex having a physiologically cleavable bond connecting the sterol to the chemical modifier, where after said administering, the bond is cleaved to release the sterol in its uncomplexed form;

wherein lower alkyl is selected from the group consisting of methyl, ethyl, n-propyl and isopropyl;

wherein alkyl is selected from the group consisting of straight or branched alkyl chains having from 4 to 20 carbons;

wherein cylcloalkyl is selected from the group consisting of cyclic alkyl ring structures having between 3 to 10 carbons;

wherein R is selected from the group consisting of straight or branched acylalkyl chains and straight or branched acylalkyl chains with additional functional group or groups present internally; wherein said functionality is selected from the group consisting of carboxy, carbonate, carbamate, and amide;

wherein R contains an oxygen atom or a nitrogen atom connected to the carbonyl carbon to provide a carbonate or carbamate linkage, respectively;

wherein the chemical modifier/17-hydroxy sterol complex enhances the iotophoretic transport compared to said 17-hydroxy sterol alone.

wherein said chemical modifier has a charge to mass ratio of at least one charge to 1000.

14. The composition of claim 1, where R and $R^1$ together with the nitrogen to which they are attached form a substituted aromatic heterocycle.

* * * * *